(12) United States Patent
Burdick et al.

(10) Patent No.: US 9,382,257 B2
(45) Date of Patent: Jul. 5, 2016

(54) SUBSTITUTED PYRROLO[2,3-B]PYRAZINES AS SERINE/THREONINE KINASE INHIBITORS

(71) Applicant: Genentech, Inc., South San Francisco, CA (US)

(72) Inventors: Daniel Burdick, Burlingame, CA (US); Huifen Chen, Burlingame, CA (US); Shumei Wang, Foster City, CA (US); Weiru Wang, Lafayette, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/688,724

(22) Filed: Apr. 16, 2015

(65) Prior Publication Data
US 2015/0218176 A1    Aug. 6, 2015

Related U.S. Application Data

(63) Continuation of application No. PCT/EP2013/071496, filed on Oct. 15, 2013.

(60) Provisional application No. 61/714,558, filed on Oct. 16, 2002.

(51) Int. Cl.
| | |
|---|---|
| *A61K 31/4985* | (2006.01) |
| *C07D 231/10* | (2006.01) |
| *C07D 241/38* | (2006.01) |
| *C07D 487/04* | (2006.01) |
| *A61K 45/06* | (2006.01) |

(52) U.S. Cl.
CPC .......... *C07D 487/04* (2013.01); *A61K 31/4985* (2013.01); *A61K 45/06* (2013.01)

(58) Field of Classification Search
CPC . A61K 31/4985; C07D 231/10; C07D 241/38
USPC .......................... 514/249; 544/350; 548/373.1
See application file for complete search history.

(56) References Cited

U.S. PATENT DOCUMENTS

| | | |
|---|---|---|
| 9,133,187 B2 | 9/2015 | Blake et al. |
| 2009/0306087 A1 | 12/2009 | Ibrahim et al. |
| 2011/0015172 A1* | 1/2011 | Penning et al. .......... 514/210.18 |

FOREIGN PATENT DOCUMENTS

| | | |
|---|---|---|
| WO | WO-2011/008830 A1 | 1/2011 |
| WO | WO-2013/020062 A1 | 2/2013 |
| WO | WO-2013/130976 A1 | 9/2013 |
| WO | WO-2014/036015 A1 | 3/2014 |
| WO | WO-2014/060395 A1 | 4/2014 |
| WO | WO-2015/085007 A1 | 6/2015 |
| WO | WO-2015/103133 A1 | 7/2015 |
| WO | WO-2015/103137 A1 | 7/2015 |

OTHER PUBLICATIONS

Jordan, V. C. Nature Reviews: Drug Discovery, 2, 2003, 205.*
Hackam, et al. JAMA, 296(14), 2006, 1731-1732.*
International Preliminary Report on Patentability mailed on Apr. 21, 2015 for PCT Application No. PCT/EP2013/071496, filed on Oct. 15, 2013, 6 pages.

* cited by examiner

*Primary Examiner* — Douglas M Willis

(57) ABSTRACT

Compounds having the formula I wherein $R^1$ and $R^2$ are as defined herein are inhibitors of ERK kinase. Also disclosed are compositions and methods for treating hyperproliferative disorders.

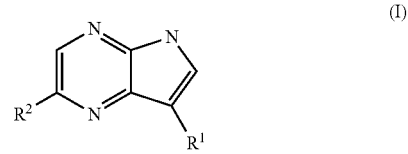

(I)

7 Claims, No Drawings

US 9,382,257 B2

SUBSTITUTED PYRROLO[2,3-B]PYRAZINES AS SERINE/THREONINE KINASE INHIBITORS

CROSS REFERENCE TO RELATED APPLICATIONS

This application is a continuation of International Patent Application No. PCT/EP2013/071496, filed on Oct. 15, 2013, which claims the benefit of priority under 35 U.S.C. §119(e) to provisional application No. 61/714,558 filed Oct. 16, 2012, the contents of which applications are incorporated by reference herein in their entirety.

FIELD OF THE INVENTION

The present invention relates to compounds which inhibit kinases and which are useful for treating hyperproliferative and neoplastic diseases by inhibiting signal transduction pathways which commonly are overactive or overexpressed in cancerous tissue. The present compounds are selective inhibitors of ERK. The present invention further relates to methods for treating cancer or hyperproliferative diseases with compounds within the scope of the present invention.

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface receptor tyrosine kinase (RTK's) such as erbB family, PDGF, FGF, and VEGF receptor tyrosine kinase. Activation of an RTK induces a cascade of phosphorylation events that begins with activation of Ras. Activation of Ras leads to the recruitment and activation of Raf, a serine-threonine kinase.

Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signaling pathway is an attractive pathway for anticancer therapies in a broad spectrum of human tumors. (M. Hohno and J. Pouyssegur, *Prog. in Cell Cycle Res.* 2003 5:219)

Therefore, small-molecular inhibitors of ERK activity (i.e., ERK1 and ERK2 activity) would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

There is a continuing need for new and novel therapeutic agents which can be used for cancer and hyperproliferative conditions. The Raf/MEK/ERK pathway is an important signaling pathway which is frequently over-expressed and/or overactive in many cancerous tissues. Design and development of new pharmaceutical compounds is essential.

SUMMARY OF THE INVENTION

In one aspect of the present invention there is provided a compound according to formula I wherein:

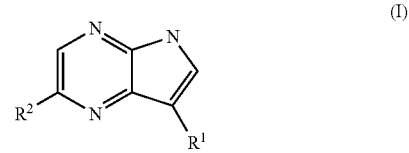

$R^1$ is an optionally substituted heteroaryl selected from the group consisting of N-aralkyl-pyrazole, pyridinyl and pyrimidinyl.

$R^2$ is an optionally substituted phenyl or optionally substituted heteraryl wherein said heteroaryl group is selected from the group consisting of pyrazolyl, imidazolyl, oxazolyl, isoxazolyl, thiazolyl, isothiazolyl, pyridinyl, pyrimidinyl, pyridazinyl, pyrazinyl, indolinyl, quinolinyl and indazolinyl. wherein each said phenyl, said aralkyl or said heteroaryl is optionally independently substituted with one to three groups selected from the group consisting of:

$C_{1-6}$ alkyl,
$C_{1-6}$ haloalkyl,
$C_{1-6}$ hydroxyalkyl,
$C_{1-6}$ alkoxy,
$C_{1-6}$ haloalkoxy,
$C_{3-6}$ cycloalkyl-$C_{1-3}$ alkoxy,
hydroxyl,
halogen,
(k) $(CH_2)_{0-3}NR^aR^b$,
(l) $X^1(CH_2)_{2-4}NR^aR^b$ wherein $X^1$ is NH or O,
(n) $NHNR^aR^b$,
(o) cyano,
(p) nitro,
(q) $CONR^aR^b$,
(r) $(CR^3_2)_{1-3}Ar$ wherein Ar is a phenyl, pyridinyl or quinolinyl optionally substituted with one to three groups independently selected from the group consisting of $C_{1-6}$ alkyl, $C_{1-3}$ haloalky, $C_{1-6}$ alkoxy, $C_{1-3}$ haloalkoxy, cyano and nitro and $R^3$ is independently in each occurrence hydrogen or $C_{1-3}$ alkyl; and,
(s) optionally substituted $O(CH_2)_{0-3}Ar$.

$R^a$ and $R^b$ are independently hydrogen or $C_{1-3}$ alkyl, $C_{3-6}$ cycloalkyl, optionally substituted benzyl, $C_{1-6}$ acyl, 5-methyl-isoxazole-3-carbonyl, 2-methyl-3H-pyrazole-3-carbonyl, 2,5-dimethyl-oxazole-4-carbonyl, pyrazine-2-carbonyl or $R^a$ and $R^b$ together with the nitrogen atom to which they are attached form a cyclic amine.

In another aspect of the present invention there is provided a pharmaceutically acceptable salt of a compound as described herein. In yet another aspect of the present invention there is provided a pharmaceutical composition comprising a compound as described herein In a further aspect of the present invention there is provided a method of inhibiting ERK activity by contacting a cell or administering an inhibitor to a mammal with a compound as described herein. In another aspect of the present invention there is provided a method for treat a hyperproliferative condition or cancer with an ERK inhibitor as described herein.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

MeC(=O)OR$^4$ wherein

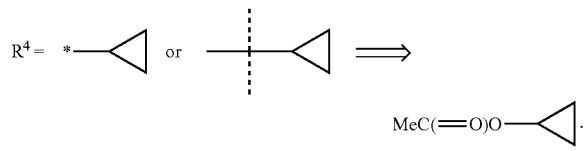

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH-⇌-C(—OH)=CH—), amide/imidic acid (—C(=O)—NH-⇌-C(—OH)=N—) and amidine (—C(=NR)—NH-⇌-C(—NHR)=N—) tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formulae I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, .alpha.-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxiliary) to produce diastereomers which can be separated by chromatography or by fractional crystallization after which time the chiral auxiliary is chemically removed to afford the pure enantiomers.

The compounds of formula I may contain a basic center and suitable acid addition salts are formed from acids which form non-toxic salts. Examples of salts of inorganic acids include the hydrochloride, hydrobromide, hydroiodide, chloride, bromide, iodide, sulfate, bisulfate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

The terms "treat" and "treatment" refer to therapeutic treatment wherein the object is to slow down (lessen) an undesired physiological change or disorder, such as the spread of cancer. For purposes of this invention, beneficial or desired clinical results include, but are not limited to, alleviation of symptoms, limiting the extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Raf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; (ix) anti-angiogenic agents such as bevacizumab (AVASTIN®), Genentech); and (x) pharmaceutically acceptable salts, acids and derivatives of any of the above.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations,* 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

The term "alkyl" as used herein without further limitation, alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, lower alkyl groups including methyl, ethyl, propyl, i-propyl, n-butyl, i-butyl, t-butyl, neopentyl, hexyl, and octyl.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl and phenylethyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to a moiety that is either an aryl or a heteroaryl group.

The term "haloalkyl" as used herein denotes an alkyl group as defined above wherein at least one hydrogen atom is substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 2-fluoroethyl, 2-chloroethyl, 2-bromoethyl, 2,2-dichloroethyl, 3-bromopropyl or 2,2,2-trifluoroethyl.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy group is the oxygen atom.

The term "haloalkoxy" as used herein refers to a group —OR where R is haloalkyl as defined herein.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers.

"Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "halo", "halogen", and "halide" are used interchangeably herein and denote fluoro, chloro, bromo, or iodo.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having two carbon atoms in common. Particular cycloalkyl groups are monocyclic. "$C_{3-7}$ cycloalkyl" as used herein refers to a cycloalkyl composed of 3 to 7 carbons in the carbocyclic ring. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "cyclic amine" denotes a saturated carbon ring, containing from 3 to 6 carbon atoms as defined above, and wherein at least one of the carbon atoms is replaced by a nitrogen atom and one or more other carbon atoms can replaced by a heteroatom selected from the group consisting of N, O or $S(O)_{0-2}$, for example, piperidine, piperazine, morpholine, thiomorpholine, di-oxo-thiomorpholine, pyrrolidine, pyrazoline, imidazolidine, azetidine. The cyclic carbon atoms are optionally substituted by one or more substituents, selected from the group consisting of halogen, hydroxy, phenyl, lower alkyl, lower alkoxy or 2-hydrogen atoms on a carbon are both replace by oxo (=O). When the cyclic amine is a piperazine, one nitrogen atom can be optionally substituted by $C_{1-6}$ alkyl, $C_{1-6}$ acyl, $C_{1-6}$ alkylsulfonyl.

(I)

In one embodiment of the present invention there is provided a compound according to formula I wherein $R^1$, $R^2$, $R^3$, $R^a$, $R^b$, Ar and $X^1$ are as defined hereinabove or a pharmaceutically acceptable salt thereof.

In another embodiment of the present invention there is provided a compound according to formula I wherein $R^1$ is optionally substituted N-benzyl-pyrazolyl or pyridinyl and $R^2$ is optionally substituted pyrazolyl, isoxazolyl, pyridinyl, pyrimidinyl, indolinyl, quinolinyl or indazolinyl.

In another embodiment of the present invention there is provided a compound according to formula I wherein $R^1$ and $R^2$ are independently optionally substituted N-benzyl-pyrazolyl or pyridinyl.

In another embodiment of the present invention there is provided a compound according to formula I wherein $R^1$ is optionally substituted N-benzyl-pyrazolyl or pyridinyl and $R^2$ is optionally substituted pyridin-4-yl or pyrazol-4-yl.

In another embodiment of the present invention there is provided a compound according to formula I wherein $R^1$ is optionally substituted $N^1$-benzyl-pyrazolyl and $R^2$ is 5-methyl-1H-pyrazol-4-yl.

In another embodiment of the present invention there is provided a compound according to formula I wherein $R^1$ is 1-(benzyl)-1H-pyrazol-4-yl, 1-(2,3-difluoro-benzyl)-1H-pyrazol-4-yl, 1-(2,4-difluoro-benzyl)-1H-pyrazol-4-yl, 1-(2, 5-difluoro-benzyl)-1H-pyrazol-4-yl, 1-(2,6-difluoro-benzyl)-1H-pyrazol-4-yl, 1-(3,4-difluoro-benzyl)-1H-pyrazol-4-yl, 1-(2,3-dichloro-benzyl)-1H-pyrazol-4-yl, 1-(2,4-dichloro-benzyl)-1H-pyrazol-4-yl, 1-(2,5-dichloro-benzyl)-1H-pyrazol-4-yl, 1-(3,4-dichloro-benzyl)-1H-pyrazol-4-yl, 1-(2,6-dichloro-benzyl)-1H-pyrazol-4-yl, 1-(4-chloro-3-fluoro-benzyl)-1H-pyrazol-4-yl, 1-(2-chloro-4-fluoro-benzyl)-1H-pyrazol-4-yl, 1-(3-chloro-4-fluoro-benzyl)-1H-pyrazol-4-yl, 1-(2-chloro-6-fluoro-benzyl)-1H-pyrazol-4-yl, 1-(2-chloro-5-fluoro-benzyl)-1H-pyrazol-4-yl, 1-(3-fluoro-2-methyl-benzyl)-1H-pyrazol-4-yl, 1-(2-fluoro-3-methyl-benzyl)-1H-pyrazol-4-yl, 1-(2-fluoro-5-methyl-benzyl)-1H-pyrazol-4-yl, 1-(4-fluoro-2-methyl-benzyl)-1H-pyrazol-4-yl, 1-(5-fluoro-2-methyl-benzyl)-1H-pyrazol-4-yl, 1-(2-fluoro-benzyl)-1H-pyrazol-4-yl, 1-(3-fluoro-benzyl)-1H-pyrazol-4-yl, 1-(4-fluoro-benzyl)-1H-pyrazol-4-yl, 1-(3-chloro-benzyl)-1H-pyrazol-4-yl, 1-(2-chloro-benzyl)-1H-pyrazol-4-yl, 1-(2-fluoro-6-methoxy-benzyl)-1H-pyrazol-4-yl, 1-(4-fluoro-3-methoxy-benzyl)-1H-pyrazol-4-yl, 1-(3-fluoro-4-methoxy-benzyl)-1H-pyrazol-4-yl, 1-(3-methoxy-benzyl)-1H-pyrazol-4-yl, 1-(4-methoxy-benzyl)-1H-pyrazol-4-yl, 1-(2-methyl-benzyl)-1H-pyrazol-4-yl, 1-(3-methyl-benzyl)-1H-pyrazol-4-yl, 1-(4-methyl-benzyl)-1H-pyrazol-4-yl, 1-(2,5-dimethyl-benzyl)-1H-pyrazol-4-yl, 1-(2-cyano-benzyl)-1H-pyrazol-4-yl, 1-(2-cyano-5-fluoro-benzyl)-1H-pyrazol-4-yl, 1-(2-nitro-benzyl)-1H-pyrazol-4-yl, 1-(2-hydroxymethyl)-1H-pyrazol-4-yl, 1-(3-fluoro-4-trifluoromethoxy-benzyl)-1H-pyrazol-4-yl, 1-(2-trifluoromethoxy-benzyl)-1H-pyrazol-4-yl, 1-(3-trifluoromethoxy-benzyl)-1H-pyrazol-4-yl, 1-(3-trifluoromethoxy-4-chloro-benzyl)-1H-pyrazol-4-yl, 1-(2-difluoromethoxy-benzyl)-1H-pyrazol-4-yl, 1-(2-trifluoromethyl-benzyl)-1H-pyrazol-4-yl, 1-(3-trifluoromethyl-benzyl)-1H-pyrazol-4-yl, 1-(2-chloro-3-trifluoromethyl-benzyl)-1H-pyrazol-4-yl, 1-(2-methyl-3-trifluoromethyl-benzyl)-1H-pyrazol-4-yl, 1-(2-chloro-3-methyl-benzyl)-1H-pyrazol-4-yl, 1-(3-trifluoromethyl-4-methoxy-benzyl)-1H-pyrazol-4-yl, 1-(3-trifluoromethyl-4-chloro-benzyl)-1H-pyrazol-4-yl, 1-(3-trifluoromethyl-2-chloro-benzyl)-1H-pyrazol-4-yl, 1-(3-trifluoromethyl-2-methyl-benzyl)-1H-pyrazol-4-yl, 1-(2-trifluoromethyl-phenyl)-ethyl]-1H-pyrazol-4-yl, 1-(3-trifluoromethoxy-benzyl)-1H-pyrazol-4-yl, 1-(3-trifluoromethoxy-benzyl)-1H-pyrazol-4-yl, 1-(2-fluoro-6-methoxy-benzyl)-1H-pyrazol-4-yl, 1-[2-(4-trifluoromethyl-phenyl)-ethyl]-1H-pyrazol-4-yl, 1-[2-(3-trifluoromethyl-phenyl)-ethyl]-1H-pyrazol-4-yl, 1-[2-(2-trifluoromethyl-phenyl)-ethyl]-1H-pyrazol-4-yl, 1-[1-(1-methyl-1-phenyl-ethyl)]-1H-pyrazol-4-yl, 1-[1-(2-chloro-phenyl)-ethyl]-1H-pyrazol-4-yl, 1-[1-(3-chloro-phenyl)-ethyl]-1H-pyrazol-4-yl, 1-[1-(2-fluoro-phenyl)-ethyl]-1H-pyrazol-4-yl, 1-[1-(3-fluoro-phenyl)-ethyl]-1H-pyrazol-4-yl, 1-[1-(4-fluoro-phenyl)-ethyl]-1H-pyrazol-4-yl, 1-[1-(2-trifluoromethyl-phenyl)-ethyl]-1H-pyrazol-4-yl, 1-[1-(2-methoxy-phenyl)-ethyl]-1H-pyrazol-4-yl, 1-[(S)-1-(2-chloro-phenyl)-ethyl]-1H-pyrazol-4-yl, quinolin-8-ylmethyl-1H-pyrazol-4-yl, pyridin-3-ylmethyl-1H-pyrazol-4-yl, pyridin-2-ylmethyl-1H-pyrazol-4-yl, 1-phenethyl-1H-pyrazol-4-yl, 1-[2-(4-trifluoromethyl-phenyl)-ethyl]-1H-pyrazol-4-yl, 1-(4-fluoro-phenyl)-ethyl]-1H-pyrazol-4-yl, 1H-pyrazol-4-yl, 1-(2-morpholin-4-yl-ethyl)-1H-pyrazol-4-yl, and 1-(1-methyl-2-phenyl-ethyl)-1H-pyrazol-4-yl In another embodiment $R^1$ is selected from the group consisting of 1-(benzyl)-1H-pyrazol-4-yl, 1-(2,4-difluoro-benzyl)-1H-pyrazol-4-yl, 1-(3-chloro-4-fluoro-benzyl)-1H-pyrazol-4-yl, 1-(2-chloro-6-fluoro-benzyl)-1H-pyrazol-4-yl, 1-(2-chloro-5-fluoro-benzyl)-1H-pyrazol-4-yl, 1-(3-fluoro-benzyl)-1H-pyrazol-4-yl, 1-(2-cyano-benzyl)-1H-pyrazol-4- yl, 1-(2-nitro-benzyl)-1H-pyrazol-4-yl, 1-(3-fluoro-4-methoxy-benzyl)-1H-pyrazol-4-yl, 1-(3-fluoro-4-trifluoromethoxy-benzyl)-1H-pyrazol-4-yl, 1-(3-trifluoromethoxy-benzyl)-1H-pyrazol-4-yl, 1-(2-fluoro-6-methoxy-benzyl)-1H-pyrazol-4-yl, 1-(1-methyl-1-phenyl-ethyl)-1H-pyrazol-4-yl, 1-(2-chloro-phenyl)-ethyl]-1H-pyrazol-4-yl, 1-[(S)-1-(2-chloro-phenyl)-ethyl]-1H-pyrazol-4-yl, quinolin-8-ylmethyl, pyridine-3-ylmethyl, 1-phenethyl-1H-pyrazol-4-yl, 1-[2-(4-trifluoromethyl-phenyl)-ethyl]-1H-pyrazol-4-yl, 1-(2-morpholin-4-yl-ethyl)-1H-pyrazol-4-yl.

In another embodiment of the present invention there is provided a compound according to formula I wherein $R^2$ is 1H-pyrazol-4-yl, 5-methyl-1H-pyrazol-4-yl, 3-methyl-1H-pyrazol-4-yl, 1-methyl-1H-pyrazol-4-yl, 3,5-dimethyl-1H-pyrazol-4-yl, 1,5-dimethyl-1H-pyrazol-4-yl, 1,3-dimethyl-1H-pyrazol-4-yl, 1,3,5-trimethyl-1H-pyrazol-4-yl, 3,5-dimethyl-isoxazol-4-yl, pyridin-4-yl, 2-methyl-pyridin-4-yl, 2-methoxy-pyridin-4-yl, 3-methoxy-pyridin-4-yl, 2-amino-pyridin-4-yl, 2-fluoro-pyridin-4-yl, 2-bromo-pyridin-5-yl, 6-piperazin-1-yl-pyridin-3-yl, 6-(4-methyl-piperazin-1-yl)-pyridin-3-yl, 1H-indazol-5-yl, 1H-indazol-6-yl, 4-fluorophenyl, 4-hydroxyphenyl, 4-hydroxymethylphenyl, 4-carboxamidophenyl, 4-methanesulfonylamino-phenyl, and 4-phenoxyphenyl In another embodiment of the present invention there is provided a compound according to formula I which compound selected from TABLE I or TABLE II or a pharmaceutically acceptable salt thereof.

In another embodiment of the present invention there is provided a method of inhibiting ERK protein kinase activity in a cell comprising treating the cell with a compound according to formula I wherein $R^1$, $R^2$, $R^3$, $R^a$, $R^b$, Ar and $X^1$ are as defined hereinabove.

In another embodiment of the present invention there is provided a method of inhibiting ERK protein kinase activity in a patient in need thereof comprising the step of administering to said patient a compound according to formula I wherein $R^1$, $R^2$, $R^3$, $R^a$, $R^b$, Ar and $X^1$ are as defined hereinabove.

In another embodiment of the present invention there is provided a method of treating or ameliorating the severity of a cancer or a hyperproliferative disorder in a patient in need thereof comprising administering to said patient a compound according to formula I wherein $R^1$, $R^2$, $R^3$, $R^a$, $R^b$, Ar and $X^1$ are as defined hereinabove.

In another embodiment of the present invention there is provided a method of treating or ameliorating the severity of a cancer or a hyperproliferative disorder selected from the group consisting of adenoma, bladder cancer, brain caner, breast cancer, colon cancer, epidermal carcinoma, follicular carcinoma, cancer of the genitourinary tract, glioblastoma, Hodgkin's disease, head and neck cancers, heptoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma in a patient in need thereof comprising administering to said patient a compound according to formula I wherein $R^1$, $R^2$, $R^3$, $R^a$, $R^b$, Ar and $X^1$ are as defined hereinabove.

In another embodiment of the present invention there is provided a method of treating or ameliorating the severity of a cancer or a hyperproliferative disorder selected from the group consisting of melanoma, pancreatic cancer, thyroid cancer colorectal cancer, lung cancer, breast cancer and ovarian cancer in a patient in need thereof comprising the step of administering to said patient a compound according to formula I wherein $R^1$, $R^2$, $R^3$, $R^a$, $R^b$, Ar and $X^1$ are as defined hereinabove.

In another embodiment of the present invention there is provided a method of treating or ameliorating the severity of a cancer or a hyperproliferative disorder selected from the group consisting of acute myelogenous leukemia, chronic myelomonocytic leukemia, chronic myelogenous leukemia, multiple myeloma, myeloid leukemia in a patient in need thereof comprising the step of administering to said patient a compound according to formula I wherein $R^1$, $R^2$, $R^3$, $R^a$, $R^b$, Ar and $X^1$ are as defined hereinabove.

In another embodiment of the present invention there is provided a method of treating or ameliorating the severity of a cancer or a hyperproliferative disorder selected from the group consisting of melanoma, pancreatic cancer, thyroid cancer colorectal cancer, lung cancer, breast cancer and ovarian cancer a in a patient in need thereof comprising the step of co-administering to said patient a compound according to formula I wherein $R^1$, $R^2$, $R^3$, $R^a$, $R^b$, Ar and $X^1$ are as defined hereinabove and at least one other chemotherapeutic agent used to treat or ameliorate a hyperproliferative disorder.

In another embodiment of the present invention there is provided a method of treating or ameliorating the severity of a cancer or a hyperproliferative disorder selected from the group consisting of acute myelogenous leukemia, chronic myelomonocytic leukemia, chronic myelogenous leukemia, multiple myeloma, myeloid leukemia in a patient in need thereof comprising the step of co-administering to said patient a compound according to formula I wherein $R^1$, $R^2$, $R^3$, $R^a$, $R^b$, Ar and $X^1$ are as defined hereinabove and at least one other chemotherapeutic agent used to treat or ameliorate a hyperproliferative disorder.

In another embodiment of the present invention there is provided a pharmaceutical composition comprising a compound according to formula I wherein $R^1$, $R^2$, $R^3$, $R^a$, $R^b$, Ar and $X^1$ are as defined hereinabove and at least one pharmaceutically acceptable excipient, carrier or diluent.

In another embodiment of the present invention there is provided a pharmaceutical composition comprising a compound according to formula I wherein $R^1$, $R^2$, $R^3$, $R^a$, $R^b$, Ar and $X^1$ are as defined hereinabove and at least one pharmaceutically acceptable excipient, carrier or diluent a further comprising a second chemotherapeutic compound.

In another embodiment of the present invention there is provided a compound according to formula I as defined hereinabove for the treatment or prophylaxis of adenoma, bladder cancer, brain cancer, breast cancer, colon cancer, epidermal carcinoma, follicular carcinoma, cancer of the genitourinary tract, glioblastoma, Hodgkin's disease, head and neck cancers, heptoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer or undifferentiated carcinoma.

In another embodiment of the present invention there is provided a compound according to formula I as defined hereinabove for the treatment or prophylaxis of melanoma, pancreatic cancer, thyroid cancer colorectal cancer, lung cancer, breast cancer or ovarian cancer.

In another embodiment of the present invention there is provided a compound according to formula I as defined hereinabove for the treatment or prophylaxis of acute myelogenous leukemia, chronic myelomonocytic leukemia, chronic myelogenous leukemia, multiple myeloma or myeloid leukemia.

In another embodiment of the present invention there is provided the use of a compound according to formula I as defined hereinabove for the treatment or prophylaxis of adenoma, bladder cancer, brain cancer, breast cancer, colon cancer, epidermal carcinoma, follicular carcinoma, cancer of the genitourinary tract, glioblastoma, Hodgkin's disease, head and neck cancers, heptoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer or undifferentiated carcinoma.

In another embodiment of the present invention there is provided the use of a compound according to formula I as defined hereinabove for the treatment or prophylaxis of melanoma, pancreatic cancer, thyroid cancer colorectal cancer, lung cancer, breast cancer or ovarian cancer.

In another embodiment of the present invention there is provided the use of a compound according to formula I as defined hereinabove for the treatment or prophylaxis of acute myelogenous leukemia, chronic myelomonocytic leukemia, chronic myelogenous leukemia, multiple myeloma or myeloid leukemia.

In another embodiment of the present invention there is provided the use of a compound according to formula I as defined hereinabove for the treatment or prophylaxis of acute myelogenous leukemia, chronic myelomonocytic leukemia, chronic myelogenous leukemia, multiple myeloma or myeloid leukemia, in combination with at least one other chemotherapeutic agent used to treat or ameliorate a hyperproliferative disorder.

In another embodiment of the present invention there is provided the use of a compound according to formula I as defined hereinabove for the preparation of medicament for the treatment or prophylaxis of adenoma, bladder cancer, brain cancer, breast cancer, colon cancer, epidermal carcinoma, follicular carcinoma, cancer of the genitourinary tract, glioblastoma, Hodgkin's disease, head and neck cancers, heptoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer or undifferentiated carcinoma.

In another embodiment of the present invention there is provided the use of a compound according to formula I as defined hereinabove for the preparation of medicament for the treatment or prophylaxis of melanoma, pancreatic cancer, thyroid cancer colorectal cancer, lung cancer, breast cancer or ovarian cancer.

In another embodiment of the present invention there is provided the use of a compound according to formula I as defined hereinabove for the preparation of medicament for the treatment or prophylaxis of acute myelogenous leukemia, chronic myelomonocytic leukemia, chronic myelogenous leukemia, multiple myeloma or myeloid leukemia.

In another embodiment of the present invention there is provided the use of a compound according to formula I as defined hereinabove for the preparation of medicament for the treatment or prophylaxis of acute myelogenous leukemia, chronic myelomonocytic leukemia, chronic myelogenous leukemia, multiple myeloma or myeloid leukemia, in combination with at least one other chemotherapeutic agent used to treat or ameliorate a hyperproliferative disorder.

Examples of representative compounds within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. The following numbering system is used herein.

TABLE 1

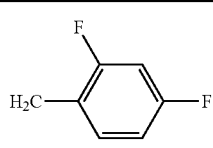

| Cpd No. | $R^{1a}$ | $R^2$ | ERK Inhibition $IC_{50}(\mu M)^1$ | RSK Inhibition $IC_{50}(\mu M)^3$ | MW | LCMS |
|---|---|---|---|---|---|---|
| I-1 | 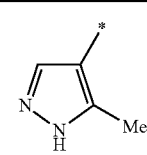 |  | 0.00123 | 0.242 | 392 | 391.38 |

TABLE 1-continued

| Cpd No. | R$^{1a}$ | R$^2$ | ERK Inhibition IC$_{50}$(μM)$^1$ | RSK Inhibition IC$_{50}$(μM)$^3$ | MW | LCMS |
|---|---|---|---|---|---|---|
| I-2 | 3-Cl, 4-F benzyl | 5-Me-1H-pyrazol-4-yl | 0.00236 | 0.276 | 408 | 407.83 |
| I-3 | 3-F benzyl | 1H-pyrazol-4-yl | 0.00275 | 0.403 | 360 | 359.3 |
| I-4 | 2-CN benzyl | 5-Me-1H-pyrazol-4-yl | 0.0013 | 0.202 | 381 | 380.41 |
| I-5 | 2-NO$_2$ benzyl | 5-Me-1H-pyrazol-4-yl | 0.0015 | 0.0972 | 401 | 400.39 |
| I-6 | 2-Cl, 6-F benzyl | 5-Me-1H-pyrazol-4-yl | 0.00184 | 0.214 | 408 | 407.83 |
| I-7 | 3-F, 4-OMe benzyl | 5-Me-1H-pyrazol-4-yl | 0.00189 | 0.34 | 404 | 403.41 |
| I-8 | 3-F, 4-OMe benzyl | 5-Me-1H-pyrazol-4-yl | 0.0025 | 0.191 | 422 | 421.4 |
| I-9 | (R)-1-(2-Cl-phenyl)ethyl | 5-Me-1H-pyrazol-4-yl | 0.0028 | 0.299 | 404 | 403.87 |

TABLE 1-continued

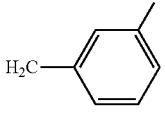

| Cpd No. | R$^{1a}$ | R$^2$ | ERK Inhibition IC$_{50}$(µM)$^1$ | RSK Inhibition IC$_{50}$(µM)$^3$ | MW | LCMS |
|---|---|---|---|---|---|---|
| I-10 | 3-fluorobenzyl | 3,5-dimethyl-1H-pyrazol-4-yl | 0.0027 | 0.387 | 388 | 387.41 |
| I-11 | 3-fluorobenzyl | pyridin-4-yl | 0.00277 | 0.501 | 371 | 370.38 |
| I-12 | 3-fluorobenzyl | 2-methylpyridin-4-yl | 0.0221$^2$ | | 385 | 384.41 |
| I-13 | CH$_2$Ph | 1,5-dimethyl-1H-pyrazol-4-yl | 0.105$^2$ | | 384 | 383.45 |
| I-14 | CH$_2$Ph | 3,5-dimethylisoxazol-4-yl | 0.11$^2$ | | 371 | 370.41 |
| I-15 | quinolin-8-ylmethyl | 5-methyl-1H-pyrazol-4-yl | 0.014 | 0.651 | 407 | 406.44 |
| I-16 | 2-fluoro-4-(trifluoromethoxy)benzyl | 5-methyl-1H-pyrazol-4-yl | 0.0179 | 0.0994 | 440 | 439.39 |
| I-17 | 2-phenylpropan-2-yl | 5-methyl-1H-pyrazol-4-yl | 0.036 | 2.3 | 384 | 383.45 |

TABLE 1-continued
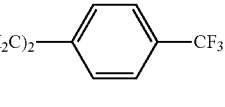
| Cpd No. | $R^{1a}$ | $R^2$ | ERK Inhibition $IC_{50}(\mu M)^1$ | RSK Inhibition $IC_{50}(\mu M)^3$ | MW | LCMS |
|---|---|---|---|---|---|---|
| I-18 | *(H2C)2—C6H4—CF3 | pyrazole-Me | 0.0444 | 50 | 438 | 437.42 |
| I-19 | CH2Ph | 6-indazolyl | 0.343[2] | | 392 | 391.43 |
| I-20 | *(CH2)2N-morpholine | 4-pyridyl | 0.416[2] | | 376 | 375.43 |
| I-21 | CH2Ph | 4-pyridyl | 0.0069 | 1.3 | 353 | 352.39 |
| I-22 | *H2C—C6H4—OCF3 | pyrazole-Me | 0.0149[2] | | 440 | 439.39 |
| I-23 | *H2C—(3-pyridyl) | 4-pyridyl | 0.0658[2] | | 354 | 353.38 |
| I-24 | *H2C—(2-Cl,5-F-C6H3) | pyrazole-Me | 0.00202 | 0.371 | 408 | 407.83 |
| I-25 | *CH(Me)—(2-Cl-C6H4) | pyrazole-Me | 0.0022 | 0.2 | 404 | 403.87 |
| I-26 | *H2C—(2-F,6-OMe-C6H3) | pyrazole-Me | 0.0034 | 0.518 | 404 | 403.41 |

TABLE 1-continued
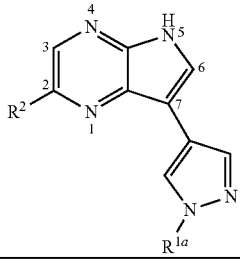
| Cpd No. | R1a | R2 | ERK Inhibition IC50(μM)[1] | RSK Inhibition IC50(μM)[3] | MW | LCMS |
|---|---|---|---|---|---|---|
| I-27 | 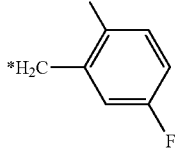 | 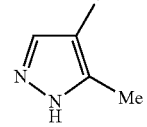 | 0.0248 | 2 | 398 | 399.1 |
[1] ERK-2 Enzymatic Assay (Example 2) unless otherwise noted
[2] LabChip Erk Assay (Example 3)
[3] P90RSK(Ser380) Phosphorylation Assay (Example 4)
TABLE II
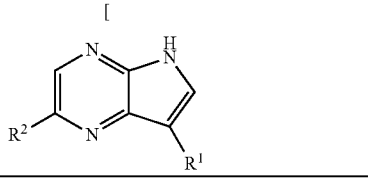
| Cpd. No. | R1 | R2 | ERK Inhibition IC50(μM)[1] | RSK Inhibition IC50(μM)[3] | MW | LCMS |
|---|---|---|---|---|---|---|
| II-1 | 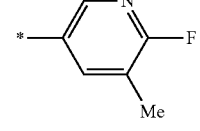 | 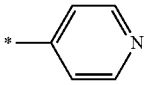 | 0.0531 LC3K | | 306 | 305.31 |
| II-2 | 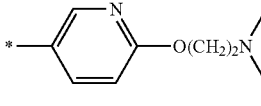 | 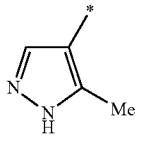 | 0.0301 | 5.7 | 406 | 405.45 |
| II-3 | 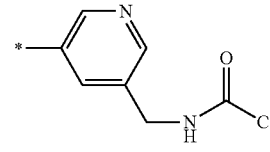 | 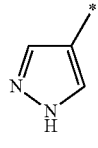 | 0.031.6 | 1.6 | 414 | 413.41 |
| II-4 | 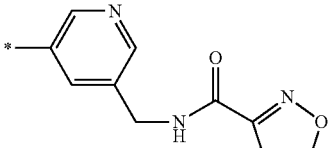 | 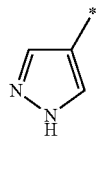 | 0.198 | 3.7 | 401 | 400.39 |

TABLE II-continued

| Cpd. No. | R¹ | R² | ERK Inhibition IC$_{50}$(μM)[1] | RSK Inhibition IC$_{50}$(μM)[3] | MW | LCMS |
|---|---|---|---|---|---|---|
| II-5 | pyridyl-CH₂-NH-C(O)-(2,5-dimethyloxazol-4-yl) | 4-pyrazolyl | 0.218 | 50 | 415 | 414.42 |
| II-6 | 2-chloro-3-methyl-pyridyl | 4-pyridyl | 0.0478[2] | | 322 | 321.76 |
| II-7 | 2-(NHCH₂Ph)-pyridyl | 3-methyl-pyrazol-4-yl | 0.0299 | 5.7 | 382 | 381.43 |
| II-8 | 2-(O-CH₂-cyclopropyl)-pyridyl | 3-methyl-pyrazol-4-yl | 0.0467 | 5.9 | 347 | 346.39 |
| II-9 | pyridyl-CH₂-NH-C(O)-(1-methyl-pyrazol-5-yl) | 4-pyrazolyl | 0.144 | 50 | 400 | 399.41 |

[1] ERK-2 Enzymatic Assay (Example 2) unless otherwise noted
[2] LabChip Erk Assay (Example 3)
[3] P90RSK(Ser380) Phosphorylation Assay (Example 4)

Compounds of the present invention can be made by a variety of methods depicted in the illustrative synthetic reaction schemes shown and described below. The starting materials and reagents used in preparing these compounds generally are either available from commercial suppliers, such as Sigma Aldrich Chemical Co., or are prepared by methods known to those skilled in the art. Generally applicable synthetic procedures have been described in treatises are set forth in references such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques. Typically such separations involve multiphase extraction, crystallization from a solvent or solvent mixture, distillation, sublimation, or chromatography. Chromatography can involve any number of methods including, for example: chiral, reverse-phase and normal phases; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Some compounds in the following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

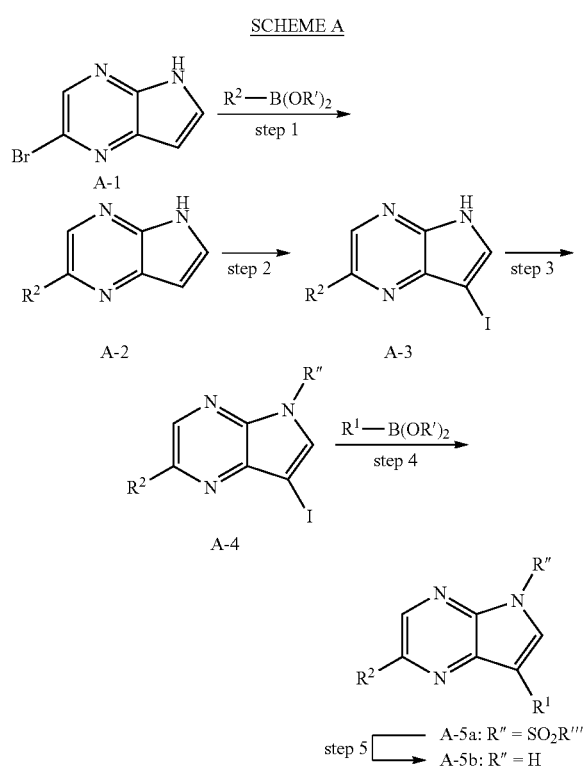

Compounds of the present invention are readily prepared form 2-bromo-5H-pyrrolo[2,3-b]pyrazine (A-1, CASRN 875781-43-4). The $R^2$ moiety is introduced utilizing the Suzuki-Miyaura reaction utilizing a (hetero)aryl boronic acid or ester (each R' is hydrogen or together, both R's are $C(Me)_2C(Me)_2$). Introduction of the C-7 substitutent is accomplished by a three-step process comprising iodination (step 2), sulfonylation of the nitrogen (step 3) and palladium-catalyzed coupling of a second heteroaryl group (step 4). Deprotection of the sulfonyl group affords compound of the present invention. The C-7 substituent also is introduced using a palladium-catalyzed coupling. The requisite heteroarylboronic acid or esters can be readily prepared by alkylation of commercially available boronic acids and esters (Scheme B)

SCHEME B

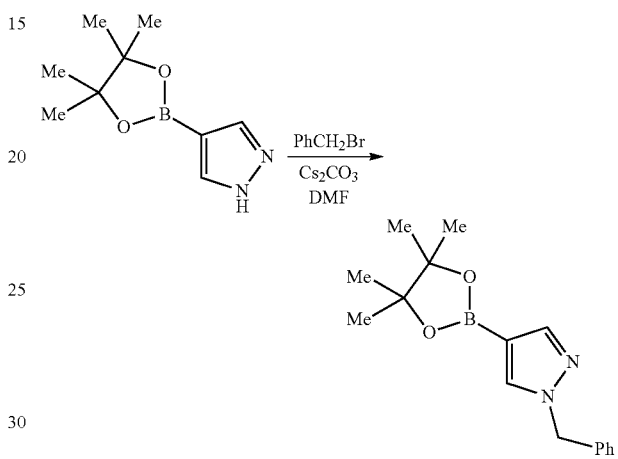

The SCHEMES described above provide general procedures which have been applied to compounds encompassed in the present invention. The examples which follow containing additional details which are useful to introduce the various structural features found in specific compounds.

Biological Activity

Determination of the activity of ERK activity of a compound of formula I is possible by a number of direct and indirect detection methods. Certain exemplary compounds described herein were assayed for their ERK inhibition assay (Example 7). The range of ERK binding activities was less than 1 nM (nanomolar) to about 10 μM (micromolar). A cell-based function assay (Example 9) was used to determine the effect of ERK inhibitors on down-stream signaling by assaying phosphorylation of P90RSK.

The cytotoxic or cytostatic activity of formula I exemplary compounds was measured by: establishing a proliferating mammalian tumor cell line in a cell culture medium, adding a formula I compound, culturing the cells for a period from about 6 h to about 5 d; and measuring cell viability (Example 8). Cell-based in vitro assays were used to measure viability, i.e. proliferation ($IC_{50}$), cytotoxicity ($EC_{50}$).

Dosage & Administration

The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of Formula I with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit ERK activity. Typically such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula I, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

A dose to treat human patients may range from about 0.1 mg to about 1000 mg of a compound of formula I. A typical dose may be about 1 mg to about 300 mg of the compound. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, H. C., et al., Ansel's *Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, R. C., *Handbook of Pharmaceutical Excipients*, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia.

Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such as sodium chloride, if desired. The solution may be filtered, e.g., using a 0.2 micron filter, to remove impurities and contaminants.

In one embodiment, the pharmaceutical composition also includes at least one additional anti-proliferative agent.

An embodiment, therefore, includes a pharmaceutical composition comprising a compound of Formula I, or a stereoisomer, tautomer or pharmaceutically acceptable salt thereof. A further embodiment includes a pharmaceutical composition comprising a compound of Formula I, or a stereoisomer, tautomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of formula I may be employed alone or in combination with other therapeutic agents for the treatment of a disease or disorder described herein, such as a hyperproliferative disorder (e.g., cancer). In certain embodiments, a compound of formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of formula I such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for any of the above co-administered agents are those presently used and may be lowered due to the combined action (synergy) of the newly identified agent and other chemotherapeutic agents or treatments.

Combination therapies according to the present invention thus comprise the administration of at least one compound of formula I, or a stereoisomer, geometric isomer, tautomer, metabolite, or pharmaceutically acceptable salt and the use of at least one other cancer treatment method. The amounts of the compound(s) of formula I and the other pharmaceutically active chemotherapeutic agent(s) and the relative timings of administration will be selected in order to achieve the desired combined therapeutic effect.

In another embodiment of the invention, an article of manufacture, or "kit", containing materials useful for the treatment of the diseases and disorders described above is provided. In one embodiment, the kit comprises a container comprising a compound of formula I, or a stereoisomer, tautomer, or pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula I or a formulation thereof which is effective for treating the condition and may have a sterile access port (for example, the container may be an intravenous solution bag or a vial having a stopper pierceable by a hypodermic injection needle). At least one active agent in the composition is a compound of formula I. Alternatively, or additionally, the article of manufacture may further comprise a second container comprising a pharmaceutical diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of formula I, such as tablets or capsules. Such a kit can include a number of unit dosages. An example of such a kit is a "blister pack". Blister packs are well known in the packaging industry and are widely used for packaging pharmaceutical unit dosage forms.

According to one embodiment, a kit may comprise (a) a first container with a compound of formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof. The referential examples that follow illustrate procedures which prepare the amines required to assemble the ERK inhibitors encompassed in the present invention.

Referential Example 1

7-iodo-2-(pyridin-4-yl)-5-tosyl-5H-pyrrolo[2,3-b]pyrazine

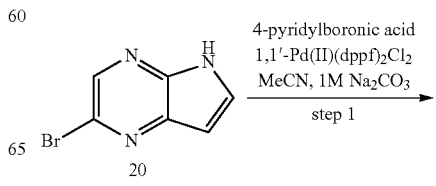

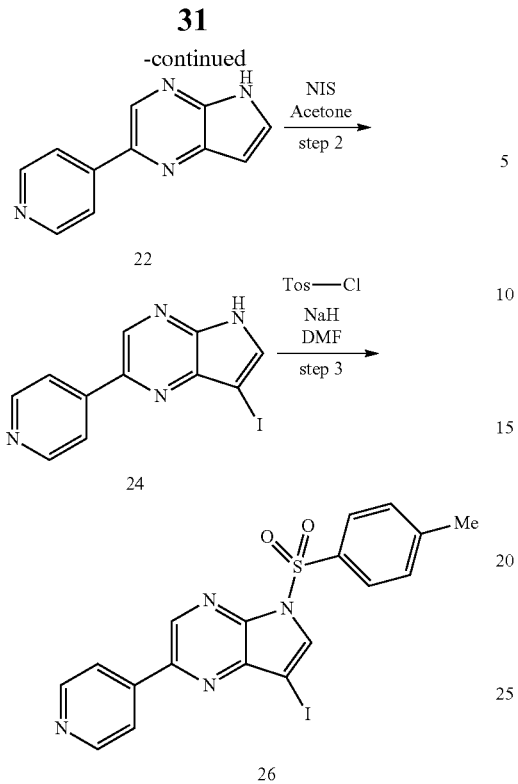

step 1: A 10 mL microwave vial was charged with 5-bromo-4,7-diazaindole (0.471 g, CASRN 875781-43-4), 4-pyridylboronic acid (0.58 g), 1M Na$_2$CO$_3$ (3 mL), 1,1'-(dppf)Pd(II)Cl$_2$ (0.097 g) and MeCN (3 mL), capped and irradiated in a microwave reactor at 150° C. for 30 min. The reaction was cooled and partitioned between H$_2$O and EtOAc. The aqueous layer was twice washed with EtOAc. The combined organic layers were washed once with brine, dried (MgSO$_4$), filtered and concentrated to afford a solid residue. The crude purified by SiO$_2$ chromatography eluting with an EtOH/EtOAc gradient (1 to 20% EtOH over 12 min) to afford 0.28 g of pure 2-(pyridin-4-yl)-5H-pyrrolo[2,3-b]pyrazin (22).

step 2: To a solution of 22 (0.35 g) and acetone (20 mL) of acetone was added in one portion N-iodosuccinimide (0.44 g). The mixture was stirred at RT for 30 min and then concentrated to afford 0.8 g of crude material. The crude product was purified by SiO$_2$ chromatography eluting with and EtOH/EtOAc gradient (1 to 15% over 15 minutes) to afford 0.36 g of pure 7-iodo-2-(pyridin-4-yl)-5H-pyrrolo[2,3-b]pyrazine (24).

step 3: A suspension of 24 (0.36 g) and DMF (10 mL) was cooled to 0° C. in an ice bath. To the suspension was added NaH (0.054 g, 60% NaH in mineral oil) in one portion and the mixture was stirred for 20 min at 0° C. To the resulting mixture was added p-TosCl (0.24 g) and the reaction was warmed to RT with stirring. After 3 h, the reaction was concentrated and partitioned between EtOAc and H$_2$O. The aqueous layer was extracted one additional time and the combined organic layers were washed with brine, dried (MgSO$_4$), filtered and concentrated down to give a solid residue. The crude product was purified by SiO$_2$ chromatography eluting with an EtOH/EtOAc gradient (1 to 15% EtOH over 11 min) to afford 0.25 g of 7-iodo-2-(pyridin-4-yl)-5-tosyl-5H-pyrrolo[2,3-b]pyrazine (26).

The following intermediates were analogously using the indicated boronic ester: 7-iodo-2-(2-methylpyridin-4-yl)-5-tosyl-5H-pyrrolo[2,3-b]pyrazine, (2-methyl-pyridin-4-yl boronic acid, CASRN 579746-63-4); 4-(7-iodo-5-tosyl-5H-pyrrolo[2,3-b]pyrazin-2-yl)pyridin-2-amine, (2-amino-pyridin-4-yl boronic acid, CASRN 903513-62-2); 7-iodo-2-(2-methoxypyridin-4-yl)-5-tosyl-5H-pyrrolo[2,3-b]pyrazine, (2-methoxy-pyridin-4-yl boronic acid, CASRN 762262-09-9); 2-(2-fluoropyridin-4-yl)-7-iodo-5-tosyl-5H-pyrrolo[2,3-b]pyrazine, (2-fluoro-pyridin-4-yl boronic acid, CASRN 401815-98-3); 2-(1,5-dimethyl-1H-pyrazol-4-yl)-7-iodo-5-tosyl-5H-pyrrolo[2,3-b]pyrazine, (B-(1,5-dimethyl-1H-pyrazol4-yl)-boronic acid, CASRN 1204333-57-2); 7-iodo-5-tosyl-2-(1,3,5-trimethyl-1H-pyrazol-4-yl)-5H-pyrrolo[2,3-b]pyrazine, (B-(1,3,5-trimethyl-1H-pyrazol-4-yl)-boronic acid, CASRN 847818-62-6); and 2-(1,3-dimethyl-1H-pyrazol-4-yl)-7-iodo-5-tosyl-5H-pyrrolo[2,3-b]pyrazine, (B-(1, 3-dimethyl-1H-pyrazol-4-yl)-boronic acid, CASRN 1146616-03-6).

Referential Example 2

7-iodo-5-tosyl-2-(1-tosyl-1H-pyrazol-4-yl)-5H-pyrrolo[2,3-b]pyrazine

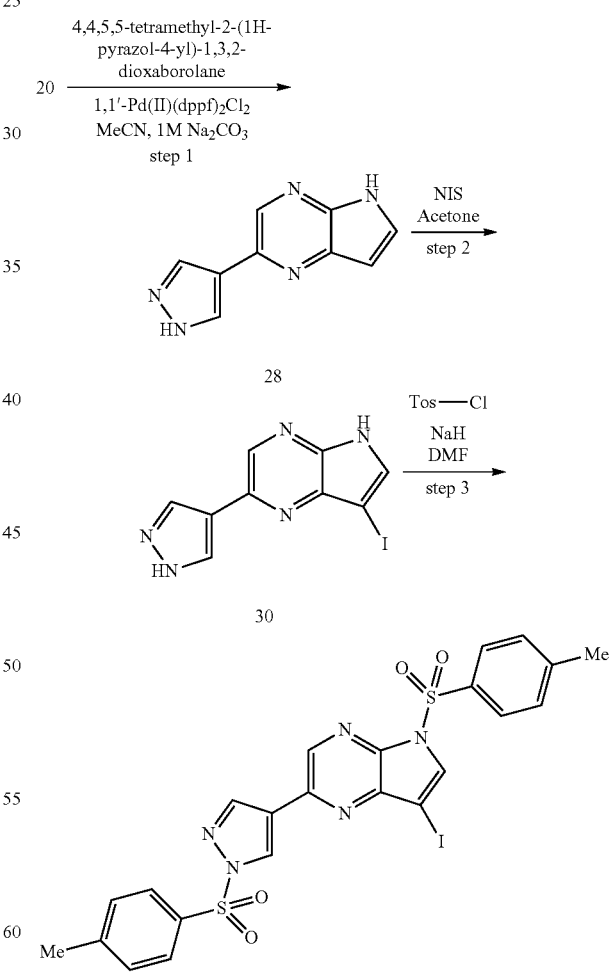

step 1: A 30 mL microwave vial was charged with 20 (1.0 g), 4,4,5,5-tetramethyl-2-(1H-pyrazol-4-yl)-1,3,2-dioxaborolane (1.08 g), 1M Na$_2$CO$_3$ (5 mL), 0.045 g of 1,1'-bis (diphenylphosphino)ferrocenepalladium (II) chloride (0.045 g) and MeCN (5 mL), capped and irradiated in a microwave reactor at 100° C. for 30 min. The reaction mixture was cooled and partitioned between H$_2$O and EtOAc. The aqueous layer was washed twice with EtOAc. The combined organic layers were washed once with brine, dried (MgSO$_4$), filtered and concentrated to afford a solid residue. The crude material was purified by SiO$_2$ chromatography eluting with and EtOH/EtOAc gradient (1 to 20% EtOH over 22 min) to afford 0.63 g of pure 2-(1H-pyrazol-4-yl)-5H-pyrrolo[2,3-b]pyrazine (28).

step 2: To a solution of 28 (0.27 g) and acetone (20 mL) was added in one portion NIS (0.36 g). The mixture was stirred at RT for 30 min and then concentrated to afford 0.55 g of crude material which was purified by SiO$_2$ chromatography using an EtOH/EtOAc gradient (1 to 15% EtOH over 15 min) to afford 0.29 g of pure 7-iodo-2-(1H-pyrazol-4-yl)-5H-pyrrolo[2,3-b]pyrazine (30).

step 3: To a solution of 30 (4.7 g) and DMF (80 mL) cooled to 0° C. in an ice bath was added portion wise NaH (1.27 g, 60% mineral oil dispersion) and the mixture was stirred for 30 min at 0° C. To the solution was added drop wise a solution of p-Tos-Cl (6.08 g) and DMF (60 mL) and the stirred solution was warmed to RT. After 18 h, the reaction was concentrated and partitioned between EtOAc and H$_2$O. The aqueous layer was extracted one additional time and the combined organic layers were washed with brine, dried (MgSO$_4$), filtered and concentrated to afford a solid residue. The crude material was purified by SiO$_2$ chromatography eluting with an EtOAc/heptane gradient (1 to 100% EtOAc over 25 min to give 2.98 g of 7-iodo-5-tosyl-2-(1-tosyl-1H-pyrazol-4-yl)-5H-pyrrolo[2,3-b]pyrazine (32).

The following intermediates were analogously using the indicated boronic ester: 2-(3,5-dimethyl-1-tosyl-1H-pyrazol-4-yl)-7-iodo-5-tosyl-5H-pyrrolo[2,3-b]pyrazine, (4,4,5,5-tetramethyl-2-(3,5-dimethyl-1H-pyrazol-4-yl)-1,3,2-dioxaborolane, CASRN 857530-80-4) and 7-iodo-2-(5-methyl-1-tosyl-1H-pyrazol-4-yl)-5-tosyl-5H-pyrrolo[2,3-b]pyrazine, (4,4,5,5-tetramethyl-2-(5-methyl-1H-pyrazol-4-yl)-1,3,2-dioxaborolane, CASRN 936250-20-3).

Referential Example 3

1-benzyl-4-(4,4,5,5-tetramethyl-1,3,2-dioxaborolan-2-yl)-1H-pyrazole 0.25 g 4-(4,4,5,5-tetramethyl-1,3,2-dioxaborolan-2-yl)-1H-pyrazole was dissolved in 5 mL of DMF and 0.63 g cesium carbonate was added. To this suspension was added 0.17 mL of benzyl bromide and the reaction was stirred overnight at room temperature. The reaction was allowed to settle and the DMF was decanted into a flask. The remaining residue was washed and decanted twice with ethyl acetate and these washes were added to the flask with the DMF. Water was added to the ethyl acetate and DMF and the organic layer removed. The aqueous layer was extracted with ethyl acetate and the combined organic layers were dried over MgSO$_4$ and concentrated to give 0.28 g of 1-benzyl-4-(4,4,5,5-tetramethyl-1,3,2-dioxaborolan-2-yl)-1H-pyrazole which was used without further purification.

The following intermediates were made in the same manner:
1-(3-fluorobenzyl)-4-(4,4,5,5-tetramethyl-1,3,2-dioxaborolan-2-yl)-1H-pyrazole; 1-(3,4-difluorobenzyl)-4-(4,4,5,5-tetramethyl-1,3,2-dioxaborolan-2-yl)-1H-pyrazole; 1-(1-phenylethyl)-4-(4,4,5,5-tetramethyl-1,3,2-dioxaborolan-2-yl)-1H-pyrazole; 1-(3-methoxybenzyl)-4-(4,4,5,5-tetramethyl-1,3,2-dioxaborolan-2-yl)-1H-pyrazole; 1-(3-chloro-4-fluorobenzyl)-4-(4,4,5,5-tetramethyl-1,3,2-dioxaborolan-2-yl)-1H-pyrazole; 1-(3,4-dichlorobenzyl)-4-(4,4,5,5-tetramethyl-1,3,2-dioxaborolan-2-yl)-1H-pyrazole; 1-(4-fluorobenzyl)-4-(4,4,5,5-tetramethyl-1,3,2-dioxaborolan-2-yl)-1H-pyrazole; 1-(3-fluorobenzyl)-4-(4,4,5,5-tetramethyl-1,3,2-dioxaborolan-2-yl)-1H-pyrazole; 1-(2-fluorobenzyl)-4-(4,4,5,5-tetramethyl-1,3,2-dioxaborolan-2-yl)-1H-pyrazole; 1-(3-methylbenzyl)-4-(4,4,5,5-tetramethyl-1,3,2-dioxaborolan-2-yl)-1H-pyrazole; 1-(3,4-dichlorobenzyl)-4-(4,4,5,5-tetramethyl-1,3,2-dioxaborolan-2-yl)-1H-pyrazole; 1-(4-methoxybenzyl)-4-(4,4,5,5-tetramethyl-1,3,2-dioxaborolan-2-yl)-1H-pyrazole; 1-(2,3-dichlorobenzyl)-4-(4,4,5,5-tetramethyl-1,3,2-dioxaborolan-2-yl)-1H-pyrazole; 1-(2,3-difluorobenzyl)-4-(4,4,5,5-tetramethyl-1,3,2-dioxaborolan-2-yl)-1H-pyrazole; 4-(4,4,5,5-tetramethyl-1,3,2-dioxaborolan-2-yl)-1-(3-(trifluoromethoxy)benzyl)-1H-pyrazole; 1-(2,4-difluorobenzyl)-4-(4,4,5,5-tetramethyl-1,3,2-dioxaborolan-2-yl)-1H-pyrazole; 1-(4-chloro-3-fluorobenzyl)-4-(4,4,5,5-tetramethyl-1,3,2-dioxaborolan-2-yl)-1H-pyrazole; 1-(4-chlorobenzyl)-4-(4,4,5,5-tetramethyl-1,3,2-dioxaborolan-2-yl)-1H-pyrazole; 1-(3-chlorobenzyl)-4-(4,4,5,5-tetramethyl-1,3,2-dioxaborolan-2-yl)-1H-pyrazole; 1-(3-chloro-4-(trifluoromethoxy)benzyl)-4-(4,4,5,5-tetramethyl-1,3,2-dioxaborolan-2-yl)-1H-pyrazole; 1-(3-fluoro-4-methoxybenzyl)-4-(4,4,5,5-tetramethyl-1,3,2-dioxaborolan-2-yl)-1H-pyrazole; 1-(4-fluoro-3-methoxybenzyl)-4-(4,4,5,5-tetramethyl-1,3,2-dioxaborolan-2-yl)-1H-pyrazole; 1-(2-chloro-5-fluorobenzyl)-4-(4,4,5,5-tetramethyl-1,3,2-dioxaborolan-2-yl)-1H-pyrazole; 1-(2-chloro-4-fluorobenzyl)-4-(4,4,5,5-tetramethyl-1,3,2-dioxaborolan-2-yl)-1H-pyrazole; 1-(2-chlorobenzyl)-4-(4,4,5,5-tetramethyl-1,3,2-dioxaborolan-2-yl)-1H-pyrazole; 4-(4,4,5,5-tetramethyl-1,3,2-dioxaborolan-2-yl)-1-(1-(3-(trifluoromethyl)phenyl)ethyl)-1H-pyrazole; 4-(4,4,5,5-tetramethyl-1,3,2-dioxaborolan-2-yl)-1-(4-(trifluoromethoxy)benzyl)-1H-pyrazole; 1-(4-methoxy-3-(trifluoromethyl)benzyl)-4-(4,4,5,5-tetramethyl-1,3,2-dioxaborolan-2-yl)-1H-pyrazole; 1-(1-(4-fluorophenyl)ethyl)-4-(4,4,5,5-tetramethyl-1,3,2-dioxaborolan-2-yl)-1H-pyrazole; 1-(2-methylbenzyl)-4-(4,4,5,5-tetramethyl-1,3,2-dioxaborolan-2-yl)-1H-pyrazole; 1-(2-nitrobenzyl)-4-(4,4,5,5-tetramethyl-1,3,2-dioxaborolan-2-yl)-1H-pyrazole; 1-(2-cyanobenzyl)-4-(4,4,5,5-tetramethyl-1,3,2-dioxaborolan-2-yl)-1H-pyrazole; 1-(2-trifluoromethylbenzyl)-4-(4,4,5,5-tetramethyl-1,3,2-dioxaborolan-2-yl)-1H-pyrazole; (2-((4-(4,4,5,5-tetramethyl-1,3,2-dioxaborolan-2-yl)-1H-pyrazol-1-yl)methyl)phenyl)methanol; 4-(4,4,5,5-tetramethyl-1,3,2-dioxaborolan-2-yl)-1-(1-(2-(trifluoromethyl)phenyl)ethyl)-1H-pyrazole; 1-(1-(2-chlorophenyl)ethyl)-4-(4,4,5,5-tetramethyl-1,3,2-dioxaborolan-2-yl)-1H-pyrazole; 4-(4,4,5,5-tetramethyl-1,3,2-dioxaborolan-2-yl)-1-(2-(trifluoromethoxy)benzyl)-1H-pyrazole; (R)-4-(4,4,5,5-tetramethyl-1,3,2-dioxaborolan-2-yl)-1-(1-(3-(trifluoromethyl)phenyl)ethyl)-1H-pyrazole; (S)-4-(4,4,5,5-tetramethyl-1,3,2-dioxaborolan-2-yl)-1-(1-(3-(trifluoromethyl)phenyl)ethyl)-1H-pyrazole; (R)-1-(1-(2-chlorophenyl)ethyl)-4-(4,4,5,5-tetramethyl-1,3,2-dioxaborolan-2-yl)-1H-pyrazole; (S)-1-(1-(2-chlorophenyl)ethyl)-4-(4,4,5,5-tetramethyl-1,3,2-dioxaborolan-2-yl)-1H-pyrazole; 1-(2-phenylpropan-2-yl)-4-(4,4,5,5-tetramethyl-1,3,2-dioxaborolan-2-yl)-1H-pyrazole; 1-(2,6-dichlorobenzyl)-4-(4,4,5,5-tetramethyl-1,3,2-dioxaborolan-2-yl)-1H-pyrazole; 1-(2-chloro-6-fluorobenzyl)-4-(4,4,5,5-tetramethyl-1,3,2-dioxaborolan-2-yl)-1H-pyrazole; 1-(2,6-difluorobenzyl)-4-(4,4,5,5-tetramethyl-1,3,2-dioxaborolan- 2-yl)-1H-pyrazole; 8-((4-(4,4,5,5-tetramethyl-1,3,2-dioxaborolan-2-yl)-1H-pyrazol-1-yl)methyl)quinoline; 1-(3-fluoro-2-methylbenzyl)-4-(4,4,5,5-tetramethyl-1,3,2-dioxaborolan-2-yl)-1H-pyrazole; 1-(4-fluoro-2-methylbenzyl)-4-(4,4,5,5-tetramethyl-1,3,2-dioxaborolan-2-yl)-1H-pyrazole; 1-(2,4-dimethylbenzyl)-4-(4,4,5,5-tetramethyl-1,3,2-dioxaborolan-2-yl)-1H-pyrazole; 1-(4-methylbenzyl)-4-(4,4,5,5-tetramethyl-1,3,2-dioxaborolan-2-yl)-1H-pyrazole; 4-(4,4,5,5-tetramethyl-1,3,2-dioxaborolan-2-yl)-1-(3-(trifluoromethyl)benzyl)-1H-pyrazole; 1-(5-fluoro-2-methylbenzyl)-4-(4,4,5,5-tetramethyl-1,3,2-dioxaborolan-2-yl)-1H-pyrazole; 1-(2,5-dichlorobenzyl)-4-(4,4,5,5-tetramethyl-1,3,2-dioxaborolan-2-yl)-1H-pyrazole; 1-(2-(difluoromethoxy)benzyl)-4-(4,4,5,5-tetramethyl-1,3,2-dioxaborolan-2-yl)-1H-pyrazole; 1-(2-fluoro-3-methylbenzyl)-4-(4,4,5,5-tetramethyl-1,3,2-dioxaborolan-2-yl)-1H-pyrazole; 1-(2,5-difluorobenzyl)-4-(4,4,5,5-tetramethyl-1,3,2-dioxaborolan-2-yl)-1H-pyrazole; 4-fluoro-2-((4-(4,4,5,5-tetramethyl-1,3,2-dioxaborolan-2-yl)-1H-pyrazol-1-yl)methyl)benzonitrile; 1-(2-fluoro-6-methoxybenzyl)-4-(4,4,5,5-tetramethyl-1,3,2-dioxaborolan-2-yl)-1H-pyrazole; 1-(2-chloro-3-(trifluoromethyl)benzyl)-4-(4,4,5,5-tetramethyl-1,3,2-dioxaborolan-2-yl)-1H-pyrazole; 4-(4,4,5,5-tetramethyl-1,3,2-dioxaborolan-2-yl)-1-(1-o-tolylethyl)-1H-pyrazole; 1-(2-methyl-3-(trifluoromethyl)benzyl)-4-(4,4,5,5-tetramethyl-1,3,2-dioxaborolan-2-yl)-1H-pyrazole; 1-(1-(2-fluorophenyl)ethyl)-4-(4,4,5,5-tetramethyl-1,3,2-dioxaborolan-2-yl)-1H-pyrazole; 1-(1-(2-methoxyphenyl)ethyl)-4-(4,4,5,5-tetramethyl-1,3,2-dioxaborolan-2-yl)-1H-pyrazole; 1-(1-(3-fluorophenyl)ethyl)-4-(4,4,5,5-tetramethyl-1,3,2-dioxaborolan-2-yl)-1H-pyrazole; 1-(1-(4-chlorophenyl)ethyl)-4-(4,4,5,5-tetramethyl-1,3,2-dioxaborolan-2-yl)-1H-pyrazole; 1-(1-(4-methylphenyl)ethyl)-4-(4,4,5,5-tetramethyl-1,3,2-dioxaborolan-2-yl)-1H-pyrazole; 1-(1-(4-trifluoromethylphenyl)ethyl)-4-(4,4,5,5-tetramethyl-1,3,2-dioxaborolan-2-yl)-1H-pyrazole; 1-(1-(2-chlorophenyl)propyl)-4-(4,4,5,5-tetramethyl-1,3,2-dioxaborolan-2-yl)-1H-pyrazole Example 1

7-(1-benzyl-1H-pyrazol-4-yl)-2-(pyridin-4-yl)-5H-pyrrolo[2,3-b]pyrazine (I-21)

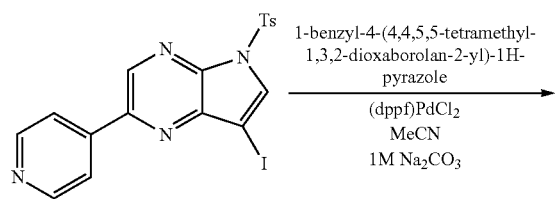

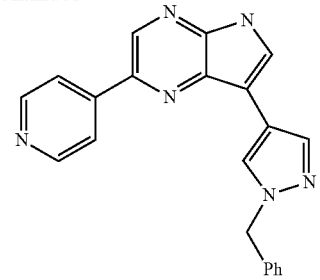

I-21

A 10 mL microwave vial was charged with 7-iodo-2-(pyridin-4-yl)-5-tosyl-5H-pyrrolo[2,3-b]pyrazine (0.1 g), 1-benzyl-4-(4,4,5,5-tetramethyl-1,3,2-dioxaborolan-2-yl))-1H-pyrazole (0.06 g), (dppf)Pd(II)Cl$_2$ (2 mg), 1M Na$_2$CO$_3$ (1 mL) and MeCN (3 mL) capped and heated in a microwave reactor for 30 min at 150° C. Water and EtOAc were added and mixture was stirred. The layers were partitioned and the aqueous layer was washed twice with EtOAc. The combined organic extracts were washed once with brine, dried (MgSO$_4$), filtered and concentrated down to afford a solid residue. The crude material was purified by reverse phase HPLC to afford 0.022 g of 7-(1-benzyl-1H-pyrazol-4-yl)-2-(pyridin-4-yl)-5H-pyrrolo[2,3-b]pyrazine.

The following pyrrolo[2,3-b]pyrazine intermediates were prepared analogously using boronic acids or boronic esters readily available from commercial sources or prepared from commercially available intermediates: 7-iodol-2-(2-methylpyridin-4-yl)-5-tosyl-5H-pyrrolo[2,3-b]pyrazine, 4-(7-iodo-5-tosyl-5H-pyrrolo[2,3-b]pyrazin-2-yl)pyridin-2-amine 2-(2-fluoropyridin-4-yl)-7-iodo-5-tosyl-5H-pyrrolo[2,3-b]pyrazine, 2-(2-methoxypyridin-4-yl)-7-iodol-5-tosyl-5H-pyrrolo[2,3-b]pyrazine.

The following compounds were prepared by the by palladium-mediated coupling of 7-iodo-pyrrolo[2,3-b]pyrazine intermediates in Example 1 and boronic acids or esters prepared as described in Referential Example 3.

7-[1-(3-fluoro-benzyl)-1H-pyrazol-4-yl]-2-pyridin-4-yl-5H-pyrrolo[2,3-b]pyrazine (I-11);
7-[1-(3-chloro-4-fluoro-benzyl)-1H-pyrazol-4-yl]-2-pyridin-4-yl-5H-pyrrolo[2,3-b]pyrazine;
7-[1-(3-methyl-benzyl)-1H-pyrazol-4-yl]-2-pyridin-4-yl-5H-pyrrolo[2,3-b]pyrazine;
7-[1-(3-fluoro-benzyl)-1H-pyrazol-4-yl]-2-(2-methyl-pyridin-4-yl)-5H-pyrrolo[2,3-b]pyrazine (I-12);
7-[1-(3,4-difluoro-benzyl)-1H-pyrazol-4-yl]-2-pyridin-4-yl-5H-pyrrolo[2,3-b]pyrazine;
4-{7-[1-(3-fluoro-benzyl)-1H-pyrazol-4-yl]-5H-pyrrolo[2,3-b]pyrazin-2-yl}-pyridin-2-ylamine;
7-[1-(4-fluoro-benzyl)-1H-pyrazol-4-yl]-2-pyridin-4-yl-5H-pyrrolo[2,3-b]pyrazine;
7-[1-(3-methoxy-benzyl)-1H-pyrazol-4-yl]-2-pyridin-4-yl-5H-pyrrolo[2,3-b]pyrazine;
7-[1-(2-fluoro-benzyl)-1H-pyrazol-4-yl]-2-pyridin-4-yl-5H-pyrrolo[2,3-b]pyrazine;
7-[1-(3-chloro-benzyl)-1H-pyrazol-4-yl]-2-pyridin-4-yl-5H-pyrrolo[2,3-b]pyrazine;
7-(1-benzyl-1H-pyrazol-4-yl)-2-(2-methyl-pyridin-4-yl)-5H-pyrrolo[2,3-b]pyrazine;
7-[1-(3-methyl-butyl)-1H-pyrazol-4-yl]-2-pyridin-4-yl-5H-pyrrolo[2,3-b]pyrazine;
7-(6-chloro-5-methyl-pyridin-3-yl)-2-pyridin-4-yl-5H-pyrrolo[2,3-b]pyrazine (II-6);

7-[1-(3,4-dichloro-benzyl)-1H-pyrazol-4-yl]-2-pyridin-4-yl-5H-pyrrolo[2,3-b]pyrazine;
7-(6-fluoro-5-methyl-pyridin-3-yl)-2-pyridin-4-yl-5H-pyrrolo[2,3-b]pyrazine; (II-1);
7-(5-methoxy-pyridin-3-yl)-2-pyridin-4-yl-5H-pyrrolo[2,3-b]pyrazine;
5-(2-pyridin-4-yl-5H-pyrrolo[2,3-b]pyrazin-7-yl)-pyridin-3-ylamine;
2-pyridin-4-yl-7-(1-pyridin-2-ylmethyl-1H-pyrazol-4-yl)-5H-pyrrolo[2,3-b]pyrazine;
7-(1-benzyl-1H-pyrazol-4-yl)-2-(2-fluoro-pyridin-4-yl)-5H-pyrrolo[2,3-b]pyrazine;
7-(6-cyclopropylmethoxy-pyridin-3-yl)-2-pyridin-4-yl-5H-pyrrolo[2,3-b]pyrazine;
(2-morpholin-4-yl-ethyl)-[5-(2-pyridin-4-yl-5H-pyrrolo[2,3-b]pyrazin-7-yl)-pyridin-2-yl]-amine;
7-(1-ethyl-1H-pyrazol-4-yl)-2-pyridin-4-yl-5H-pyrrolo[2,3-b]pyrazine;
7-(1-benzyl-1H-pyrazol-4-yl)-2-(2-methoxy-pyridin-4-yl)-5H-pyrrolo[2,3-b]pyrazine;
7-(6-benzyloxy-pyridin-3-yl)-2-pyridin-4-yl-5H-pyrrolo[2,3-b]pyrazine;
7-(6-methoxy-pyridin-3-yl)-2-pyridin-4-yl-5H-pyrrolo[2,3-b]pyrazine;
7-(6-fluoro-pyridin-3-yl)-2-pyridin-4-yl-5H-pyrrolo[2,3-b]pyrazine;
7-(1H-pyrazol-4-yl)-2-pyridin-4-yl-5H-pyrrolo[2,3-b]pyrazine;
2-pyridin-4-yl-7-pyridin-3-yl-5H-pyrrolo[2,3-b]pyrazine;
7-(5-fluoro-pyridin-3-yl)-2-pyridin-4-yl-5H-pyrrolo[2,3-b]pyrazine;
7-[1-(2-morpholin-4-yl-ethyl)-1H-pyrazol-4-yl]-2-pyridin-4-yl-5H-pyrrolo[2,3-b]pyrazine (I-20);
7-(2-fluoro-pyridin-3-yl)-2-pyridin-4-yl-5H-pyrrolo[2,3-b]pyrazine;
5'-(2-pyridin-4-yl-5H-pyrrolo[2,3-b]pyrazin-7-yl)-3,4,5,6-tetrahydro-2H-[1,2']bipyridinyl;
7-(2-chloro-pyridin-3-yl)-2-pyridin-4-yl-5H-pyrrolo[2,3-b]pyrazine;
7-(6-methyl-pyridin-3-yl)-2-pyridin-4-yl-5H-pyrrolo[2,3-b]pyrazine;
3-[4-(2-pyridin-4-yl-5H-pyrrolo[2,3-b]pyrazin-7-yl)-pyrazol-1-yl]-propan-1-ol;
7-(6-morpholin-4-yl-pyridin-3-yl)-2-pyridin-4-yl-5H-pyrrolo[2,3-b]pyrazine;
5-(2-pyridin-4-yl-5H-pyrrolo[2,3-b]pyrazin-7-yl)-pyridin-2-ylamine;
7-(2H-pyrazol-3-yl)-2-pyridin-4-yl-5H-pyrrolo[2,3-b]pyrazine; and,
7-(1-methyl-1H-pyrazol-4-yl)-2-pyridin-4-yl-5H-pyrrolo[2,3-b]pyrazine.

Similarly, 2-(1H-indazol-5-yl)-7-pyridin-3-yl-5H-pyrrolo[2,3-b]pyrazine was prepared from 2-(1H-indazol-5-yl)-7-iodo-5-tosyl-5H-pyrrolo[2,3-b]pyrazine; 7-(1-benzyl-1H-pyrazol-4-yl)-2-(1H-indazol-6-yl)-5H-pyrrolo[2,3-b]pyrazine (I-19) was prepared from 2-(1H-indazol-6-yl)-7-iodo-5-tosyl-5H-pyrrolo[2,3-b]pyrazine; and, 3-(7-pyridin-3-yl-5H-pyrrolo[2,3-b]pyrazin-2-yl)-quinoline was prepared from 3-(7-iodo-5-tosyl-5H-pyrrolo[2,3-b]pyrazin-2-yl)quinoline utilizing a pyridin-3-yl boronic acid.

The following compounds were prepared analogously by coupling 32 and the appropriate boronic acid or ester:
7-(1-benzyl-1H-pyrazol-4-yl)-2-(1H-pyrazol-4-yl)-5H-pyrrolo[2,3-b]pyrazine;
7-[1-(3-fluoro-benzyl)-1H-pyrazol-4-yl]-2-(1H-pyrazol-4-yl)-5H-pyrrolo[2,3-b]pyrazine (I-3);
2-(1H-pyrazol-4-yl)-7-pyridin-3-yl-5H-pyrrolo[2,3-b]pyrazine;
4-fluoro-N-{5-[2-(1H-pyrazol-4-yl)-5H-pyrrolo[2,3-b]pyrazin-7-yl]-pyridin-3-ylmethyl}-benzamide (II-3);
3-fluoro-N-{5-[2-(1H-pyrazol-4-yl)-5H-pyrrolo[2,3-b]pyrazin-7-yl]-pyridin-3-ylmethyl}-benzamide;
2-methyl-2H-pyrazole-3-carboxylic acid {5-[2-(1H-pyrazol-4-yl)-5H-pyrrolo[2,3-b]pyrazin-7-yl]-pyridin-3-ylmethyl}-amide (II-9);
pyrazine-2-carboxylic acid {5-[2-(1H-pyrazol-4-yl)-5H-pyrrolo[2,3-b]pyrazin-7-yl]-pyridin-3-ylmethyl}-amide; and
2,5-dimethyl-oxazole-4-carboxylic acid {5-[2-(1H-pyrazol-4-yl)-5H-pyrrolo[2,3-b]pyrazin-7-yl]-pyridin-3-ylmethyl}-amide (II-5).

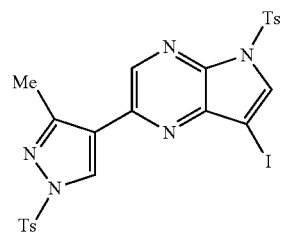

35a

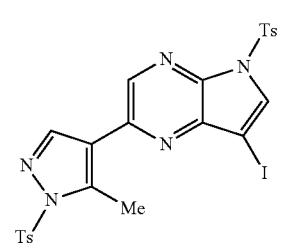

35b

The following compounds were prepared analogously by coupling 7-iodo-5-tosyl-2-(1-tosyl-3-methyl-1H-pyrazol-4-yl)-5H-pyrrolo[2,3-b]pyrazine (35a) or 7-iodo-5-tosyl-2-(1-tosyl-3-methyl-1H-pyrazol-4-yl)-5H-pyrrolo[2,3-b]pyrazine (35b) and the appropriate boronic acid or ester using commercially available boronic acids, boronic esters or boronic acids or esters available from commercial intermediates:
7-[1-(2,4-difluoro-benzyl)-1H-pyrazol-4-yl]-2-(5-methyl-1H-pyrazol-4-yl)-5H-pyrrolo[2,3-b]pyrazine (I-1);
7-[1-(3-chloro-4-fluoro-benzyl)-1H-pyrazol-4-yl]-2-(5-methyl-1H-pyrazol-4-yl)-5H-pyrrolo[2,3-b]pyrazine (I-2);
7-[1-(3-fluoro-benzyl)-1H-pyrazol-4-yl]-2-(5-methyl-1H-pyrazol-4-yl)-5H-pyrrolo[2,3-b]pyrazine;
7-[1-(4-fluoro-benzyl)-1H-pyrazol-4-yl]-2-(5-methyl-1H-pyrazol-4-yl)-5H-pyrrolo[2,3-b]pyrazine;
7-[1-(4-methoxy-benzyl)-1H-pyrazol-4-yl]-2-(5-methyl-1H-pyrazol-4-yl)-5H-pyrrolo[2,3-b]pyrazine;
7-(1-benzyl-1H-pyrazol-4-yl)-2-(3-methyl-1H-pyrazol-4-yl)-5H-pyrrolo[2,3-b]pyrazine;
2-(5-methyl-1H-pyrazol-4-yl)-7-[1-(3-trifluoromethoxy-benzyl)-1H-pyrazol-4-yl]-5H-pyrrolo[2,3-b]pyrazine (I-22);
7-[1-(3,4-dichloro-benzyl)-1H-pyrazol-4-yl]-2-(5-methyl-1H-pyrazol-4-yl)-5H-pyrrolo[2,3-b]pyrazine;
7-[1-(2,3-dichloro-benzyl)-1H-pyrazol-4-yl]-2-(5-methyl-1H-pyrazol-4-yl)-5H-pyrrolo[2,3-b]pyrazine;
7-(5-methyl-pyridin-3-yl)-2-pyridin-4-yl-5H-pyrrolo[2,3-b]pyrazine;
4-[7-(1-benzyl-1H-pyrazol-4-yl)-5H-pyrrolo[2,3-b]pyrazin-2-yl]-pyridin-2-ylamine;

2-pyridin-4-yl-7-(1-pyridin-3-ylmethyl-1H-pyrazol-4-yl)-5H-pyrrolo[2,3-b]pyrazine (I-23);
7-(1-propyl-1H-pyrazol-4-yl)-2-pyridin-4-yl-5H-pyrrolo[2,3-b]pyrazine;
7-[1-(2-methyl-benzyl)-1H-pyrazol-4-yl]-2-(5-methyl-1H-pyrazol-4-yl)-5H-pyrrolo[2,3-b]pyrazine;
2-{4-[2-(5-methyl-1H-pyrazol-4-yl)-5H-pyrrolo[2,3-b]pyrazin-7-yl]-pyrazol-1-ylmethyl}-benzonitrile (I-4);
1-benzyl-4-[2-(5-methyl-1H-pyrazol-4-yl)-5H-pyrrolo[2,3-b]pyrazin-7-yl]-1H-pyridin-2-one;
1-[(S)-1-(4-chloro-3-fluoro-phenyl)-2-hydroxy-ethyl]-4-[2-(5-methyl-1H-pyrazol-4-yl)-5H-pyrrolo[2,3-b]pyrazin-7-yl]-1H-pyridin-2-one;
2-(5-methyl-1H-pyrazol-4-yl)-7-[1-(2-nitro-benzyl)-1H-pyrazol-4-yl]-5H-pyrrolo[2,3-b]pyrazine (I-5);
7-[1-(2-chloro-benzyl)-1H-pyrazol-4-yl]-2-(5-methyl-1H-pyrazol-4-yl)-5H-pyrrolo[2,3-b]pyrazine;
7-[1-(2-chloro-6-fluoro-benzyl)-1H-pyrazol-4-yl]-2-(5-methyl-1H-pyrazol-4-yl)-5H-pyrrolo[2,3-b]pyrazine (I-6);
7-[1-(3-chloro-benzyl)-1H-pyrazol-4-yl]-2-(5-methyl-1H-pyrazol-4-yl)-5H-pyrrolo[2,3-b]pyrazine;
7-[1-(3-fluoro-4-methoxy-benzyl)-1H-pyrazol-4-yl]-2-(5-methyl-1H-pyrazol-4-yl)-5H-pyrrolo[2,3-b]pyrazine (I-7);
7-[1-(2-chloro-5-fluoro-benzyl)-1H-pyrazol-4-yl]-2-(5-methyl-1H-pyrazol-4-yl)-5H-pyrrolo[2,3-b]pyrazine (I-24);
7-{1-[1-(2-chloro-phenyl)-ethyl]-1H-pyrazol-4-yl}-2-(5-methyl-1H-pyrazol-4-yl)-5H-pyrrolo[2,3-b]pyrazine (I-25);
7-[1-(2-fluoro-benzyl)-1H-pyrazol-4-yl]-2-(5-methyl-1H-pyrazol-4-yl)-5H-pyrrolo[2,3-b]pyrazine;
7-[1-(3-fluoro-2-methyl-benzyl)-1H-pyrazol-4-yl]-2-(5-methyl-1H-pyrazol-4-yl)-5H-pyrrolo[2,3-b]pyrazine;
7-[1-(2-difluoromethoxy-benzyl)-1H-pyrazol-4-yl]-2-(5-methyl-1H-pyrazol-4-yl)-5H-pyrrolo[2,3-b]pyrazine (I-8);
7-{1-[1-(4-fluoro-phenyl)-ethyl]-1H-pyrazol-4-yl}-2-(5-methyl-1H-pyrazol-4-yl)-5H-pyrrolo[2,3-b]pyrazine;
7-[1-(2-chloro-4-fluoro-benzyl)-1H-pyrazol-4-yl]-2-(5-methyl-1H-pyrazol-4-yl)-5H-pyrrolo[2,3-b]pyrazine;
7-{1-[(S)-1-(2-chloro-phenyl)-ethyl]-1H-pyrazol-4-yl}-2-(5-methyl-1H-pyrazol-4-yl)-5H-pyrrolo[2,3-b]pyrazine (I-9);
(2-{4-[2-(5-methyl-1H-pyrazol-4-yl)-5H-pyrrolo[2,3-b]pyrazin-7-yl]-pyrazol-1-ylmethyl}-phenyl)-methanol;
7-[1-(2,3-difluoro-benzyl)-1H-pyrazol-4-yl]-2-(5-methyl-1H-pyrazol-4-yl)-5H-pyrrolo[2,3-b]pyrazine;
7-[1-(2-fluoro-6-methoxy-benzyl)-1H-pyrazol-4-yl]-2-(5-methyl-1H-pyrazol-4-yl-5H-pyrrolo[2,3-b]pyrazine (I-26);
2-(5-methyl-1H-pyrazol-4-yl)-7-[1-(1-phenyl-ethyl)-1H-pyrazol-4-yl]-5H-pyrrolo[2,3-b]pyrazine;
7-[1-(3-methoxy-benzyl)-1H-pyrazol-4-yl]-2-(5-methyl-1H-pyrazol-4-yl)-5H-pyrrolo[2,3-b]pyrazine;
7-[1-(4-chloro-benzyl)-1H-pyrazol-4-yl]-2-(5-methyl-1H-pyrazol-4-yl)-5H-pyrrolo[2,3-b]pyrazine;
1-(3-chloro-benzyl)-4-[2-(5-methyl-1H-pyrazol-4-yl)-5H-pyrrolo[2,3-b]pyrazin-7-yl]-1H-pyridin-2-one;
7-[1-(3-methyl-benzyl)-1H-pyrazol-4-yl]-2-(5-methyl-1H-pyrazol-4-yl)-5H-pyrrolo[2,3-b]pyrazine;
7-{1-[1-(2-methoxy-phenyl)-ethyl]-1H-pyrazol-4-yl}-2-(5-methyl-1H-pyrazol-4-yl)-5H-pyrrolo[2,3-b]pyrazine;
7-[1-(3,4-difluoro-benzyl)-1H-pyrazol-4-yl]-2-(5-methyl-1H-pyrazol-4-yl)-5H-pyrrolo[2,3-b]pyrazine;
7-[1-(2,5-difluoro-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-[1-(2-trifluoromethoxy-benzyl)-1H-pyrazol-4-yl]-5H-pyrrolo[2,3-b]pyrazine;
7-[1-(4-fluoro-3-methoxy-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-[1-(3-trifluoromethyl-benzyl)-1H-pyrazol-4-yl]-5H-pyrrolo[2,3-b]pyrazine;
2-(5-methyl-1H-pyrazol-4-yl)-7-[1-(2-trifluoromethyl-benzyl)-1H-pyrazol-4-yl]-5H-pyrrolo[2,3-b]pyrazine;
7-[1-(4-fluoro-2-methyl-benzyl)-1H-pyrazol-4-yl]-2-(5-methyl-1H-pyrazol-4-yl)-5H-pyrrolo[2,3-b]pyrazine;
7-[1-(1-methyl-2-phenyl-ethyl)-1H-pyrazol-4-yl]-2-(3-methyl-1H-pyrazol-4-yl)-5H-pyrrolo[2,3-b]pyrazine;
7-[1-(2,5-dichloro-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-{1-[(R)-1-(3-trifluoromethyl-phenyl)-ethyl]-1H-pyrazol-4-yl}-5H-pyrrolo[2,3-b]pyrazine;
7-[1-(4-chloro-3-fluoro-benzyl)-1H-pyrazol-4-yl]-2-(5-methyl-1H-pyrazol-4-yl)-5H-pyrrolo[2,3-b]pyrazine;
pentanoic acid {5-[2-(1H-pyrazol-4-yl)-5H-pyrrolo[2,3-b]pyrazin-7-yl]-pyridin-3-ylmethyl}-amide;
7-[1-(2,6-difluoro-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-{1-[1-(3-trifluoromethyl-phenyl)-ethyl]-1H-pyrazol-4-yl}-5H-pyrrolo[2,3-b]pyrazine;
7-[1-(2-fluoro-3-methyl-benzyl)-1H-pyrazol-4-yl]-2-(5-methyl-1H-pyrazol-4-yl)-5H-pyrrolo[2,3-b]pyrazine;
7-{1-[1-(2-fluoro-phenyl)-ethyl]-1H-pyrazol-4-yl}-2-(5-methyl-1H-pyrazol-4-yl)-5H-pyrrolo[2,3-b]pyrazine;
7-[1-(5-fluoro-2-methyl-benzyl)-1H-pyrazol-4-yl]-2-(5-methyl-1H-pyrazol-4-yl)-5H-pyrrolo[2,3-b]pyrazine;
7-{1-[(R)-1-(2-chloro-phenyl)-ethyl]-1H-pyrazol-4-yl}-2-(5-methyl-1H-pyrazol-4-yl)-5H-pyrrolo[2,3-b]pyrazine;
8-{4-[2-(5-methyl-1H-pyrazol-4-yl)-5H-pyrrolo[2,3-b]pyrazin-7-yl]-pyrazol-1-ylmethyl}-quinoline (I-15);
2-(5-methyl-1H-pyrazol-4-yl)-7-[1-(1-p-tolyl-ethyl)-1H-pyrazol-4-yl]-5H-pyrrolo[2,3-b]pyrazine;
2-(5-methyl-1H-pyrazol-4-yl)-7-{1-[1-(2-trifluoromethyl-phenyl)-ethyl]-1H-pyrazol-4-yl}-5H-pyrrolo[2,3-b]pyrazine;
1-[1-(3-chloro-phenyl)-ethyl]-4-[2-(5-methyl-1H-pyrazol-4-yl)-5H-pyrrolo[2,3-b]pyrazin-7-yl]-1H-pyridin-2-one;
2-(5-methyl-1H-pyrazol-4-yl)-7-[1-(4-trifluoromethoxy-benzyl)-1H-pyrazol-4-yl]-5H-pyrrolo[2,3-b]pyrazine (I-16);
7-[1-(4-methyl-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-[1-(1-o-tolyl-ethyl)-1H-pyrazol-4-yl]-5H-pyrrolo[2,3-b]pyrazine;
7-[1-(4-methoxy-3-trifluoromethyl-benzyl)-1H-pyrazol-4-yl]-2-(5-methyl-1H-pyrazol-4-yl)-5H-pyrrolo[2,3-b]pyrazine;
7-{1-[1-(4-chloro-phenyl)-ethyl]-1H-pyrazol-4-yl}-2-(5-methyl-1H-pyrazol-4-yl)-5H-pyrrolo[2,3-b]pyrazine;
4-fluoro-2-{4-[2-(5-methyl-1H-pyrazol-4-yl)-5H-pyrrolo[2,3-b]pyrazin-7-yl]-pyrazol-1-ylmethyl}-benzonitrile (I-27);
7-[1-(2,6-dichloro-benzyl)-1H-pyrazol-4-yl]-2-5-methyl-1H-pyrazol-4-yl)-5H-pyrrolo[2,3-b]pyrazine;
benzyl-{5-[2-(5-methyl-1H-pyrazol-4-yl)-5H-pyrrolo[2,3-b]pyrazin-7-yl]-pyridin-2-yl}-amine; ##II-7
2-(5-methyl-1H-pyrazol-4-yl)-7-[6-(2-morpholin-4-yl-ethoxy)-pyridin-3-yl]-5H-pyrrolo[2,3-b]pyrazine (II-2);
7-[1-(2,4-dimethyl-benzyl)-1H-pyrazol-4-yl]-2-(5-methyl-1H-pyrazol-4-yl)-5H-pyrrolo[2,3-b]pyrazine;

2-(5-methyl-1H-pyrazol-4-yl)-7-{1-[(S)-1-(3-trifluoromethyl-phenyl)-ethyl]-1H-pyrazol-4-yl}-5H-pyrrolo[2,3-b]pyrazine 7-[1-(1-methyl-1-phenyl-ethyl)-1H-pyrazol-4-yl]-2-(3-methyl-1H-pyrazol-4-yl)-5H-pyrrolo[2,3-b]pyrazine (I-17);

2-(3-methyl-1H-pyrazol-4-yl)-7-{1-[2-(4-trifluoromethyl-phenyl)-ethyl]-1H-pyrazol-4-yl}-5H-pyrrolo[2,3-b]pyrazine (I-18);

7-{1-[1-(3-fluoro-phenyl)-ethyl]-1H-pyrazol-4-yl}-2-(5-methyl-1H-pyrazol-4-yl)-5H-pyrrolo[2,3-b]pyrazine;

7-(6-cyclopropylmethoxy-pyridin-3-yl)-2-(5-methyl-1H-pyrazol-4-yl)-5H-pyrrolo[2,3-b]pyrazine;

2-(3-methyl-1H-pyrazol-4-yl)-7-{1-[2-(3-trifluoromethyl-phenyl)-ethyl]-1H-pyrazol-4-yl}-5H-pyrrolo[2,3-b]pyrazine;

{5-[2-(5-methyl-1H-pyrazol-4-yl)-5H-pyrrolo[2,3-b]pyrazin-7-yl]-pyridin-2-yl}-morpholin-4-yl-amine;

2-(3-methyl-1H-pyrazol-4-yl)-7-{1-[2-(2-trifluoromethyl-phenyl)-ethyl]-1H-pyrazol-4-yl}-5H-pyrrolo[2,3-b]pyrazine;

7-[1-(2-chloro-3-trifluoromethyl-benzyl)-1H-pyrazol-4-yl]-2-(5-methyl-1H-pyrazol-4-yl)-5H-pyrrolo[2,3-b]pyrazine;

2-(5-methyl-1H-pyrazol-4-yl)-7-[1-(2-methyl-3-trifluoromethyl-benzyl)-1H-pyrazol-4-yl]-5H-pyrrolo[2,3-b]pyrazine;

7-[1-(4-chloro-3-trifluoromethoxy-benzyl)-1H-pyrazol-4-yl]-2-(5-methyl-1H-pyrazol-4-yl)-5H-pyrrolo[2,3-b]pyrazine;

benzyl-methyl-{5-[2-(5-methyl-1H-pyrazol-4-yl)-5H-pyrrolo[2,3-b]pyrazin-7-yl]-pyridin-2-yl}-amine;

7-(6-benzyloxy-pyridin-3-yl)-2-(5-methyl-1H-pyrazol-4-yl)-5H-pyrrolo[2,3-b]pyrazine; and, (4-methyl-benzyl)-{5-[2-(5-methyl-1H-pyrazol-4-yl)-5H-pyrrolo[2,3-b]pyrazin-7-yl]-pyridin-2-yl}-amine.

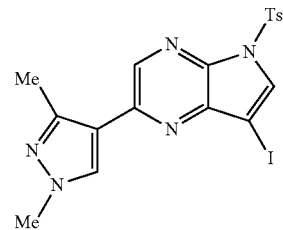

35c

The following compounds were prepared analogously by coupling 7-iodo-5-tosyl-2-(1-methyl-1H-pyrazol-4-yl)-5H-pyrrolo[2,3-b]pyrazine (35c) and the appropriate boronic acid or ester:

7-[1-(3-fluoro-benzyl)-1H-pyrazol-4-yl]-2-(1-methyl-1H-pyrazol-4-yl)-5H-pyrrolo[2,3-b]pyrazine;

7-(1-benzyl-1H-pyrazol-4-yl)-2-(1-methyl-1H-pyrazol-4-yl)-5H-pyrrolo[2,3-b]pyrazine; and, 2-(1-methyl-1H-pyrazo-4-yl)-7-pyridin-3-yl-5H-pyrrolo[2,3-b]pyrazine.

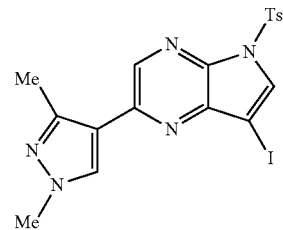

35d

The following compounds were prepared analogously by coupling 7-iodo-5-tosyl-2-(1,3-dimethyl-1H-pyrazol-4-yl)-5H-pyrrolo[2,3-b]pyrazine (35d) and the appropriate boronic acid or ester:

7-(1-benzyl-1H-pyrazol-4-yl)-2-(1,3-dimethyl-1H-pyrazol-4-yl)-5H-pyrrolo[2,3-b]pyrazine; and, 2-(1,3-dimethyl-1H-pyrazol-4-yl)-7-[1-(3-fluoro-benzyl)-1H-pyrazol-4-yl]-5H-pyrrolo[2,3-b]pyrazine.

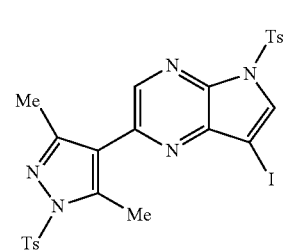

35e

The following compounds were prepared analogously by coupling 7-iodo-5-tosyl-2-(1-tosyl-3,5-dimethyl-1H-pyrazol-4-yl)-5H-pyrrolo[2,3-b]pyrazine (35e) and the appropriate boronic acid or ester:

2-(3,5-dimethyl-1H-pyrazol-4-yl)-7-[1-(3-fluoro-benzyl)-1H-pyrazol-4-yl]-5H-pyrrolo[2,3-b]pyrazine (I-10);

7-(1-benzyl-1H-pyrazol-4-yl)-2-(3,5-dimethyl-1H-pyrazol-4-yl)-5H-pyrrolo[2,3-b]pyrazine; and, 7-(1-benzyl-1H-pyrazol-4-yl)-2-(3,5-dimethyl-isoxazol-4-yl)-5H-pyrrolo[2,3-b]pyrazine (I-14).

7-(1-Benzyl-1H-pyrazol-4-yl)-2-(1,5-dimethyl-1H-pyrazol-4-yl)-5H-pyrrolo[2,3-b]pyrazine, 7-(1-benzyl-1H-pyrazol-4-yl)-2-(1,3,5-trimethyl-1H-pyrazol-4-yl)-5H-pyrrolo[2,3-b]pyrazine (I-13) and 2,7-bis-(1-benzyl-1H-pyrazol-4-yl)-5H-pyrrolo[2,3-b]pyrazine were prepared from 7-iodo-5-tosyl-2-(1,5-dimethyl-1H-pyrazol-4-yl)-5H-pyrrolo[2,3-b]pyrazine, 7-iodo-5-tosyl-2-(1,3,5-trimethyl-1H-pyrazol-4-yl)-5H-pyrrolo[2,3-b]pyrazine and 7-iodo-5-tosyl-2-(1-benzyl-1H-pyrazol-4-yl)-5H-pyrrolo[2,3-b]pyrazine, respectively.

[4-(7-Pyridin-3-yl-5H-pyrrolo[2,3-b]pyrazin-2-yl)-phenyl]-methanol and 7-[1-(3-fluorobenzyl)-1H-pyrazol-4-yl]-2-(4-fluoro-phenyl)-5H-pyrrolo[2,3-b]pyrazine were prepared from (4-(7-iodo-5-tosyl-5H-pyrrolo[2,3-b]pyrazin-2-yl)phenyl)methanol and 2-(4-fluorophenyl)-7-iodo-5-tosyl-5H-pyrrolo[2,3-b]pyrazine, respectively.

Example 2

ERK-2 Enzymatic Assay

Compounds were tested in an enzymatic assay using human ERK-2 (Mitogen Activated Kinase 1), recombinantly expressed as an n-terminal 6-His fusion protein in *E. coli* and corresponding to aa 8-360. The substrate used was the fluorescent Omnia peptide S/T17 (Invitrogen of Carlsbad, Calif.; Cat. KNZ1171C). Test compounds were diluted in DMSO in 3-fold serial dilutions at 100× final concentrations. In addition to compound, the assay contained 50 mM HEPES [pH 7.3], 10 mM MgCl2, 1 mM DTT, 0.005% Triton-X100, 5 nM ERK-2 enzyme, 6.2504 S/T17 peptide substrate and 25 µMATP (corresponding to the observed $K_m$) for a total reaction volume of 25 µL. The assay was run at ambient temperature in a white 384-well polypropylene plate (Nunc, Inc of Naperville, Ill.; Cat. 267462) collecting data every 50 seconds for approximately 30 minutes on an Envision plate reader (PerkinElmer, Inc. of Waltham, Mass.); Excitation 340 nm/Emission 495 nm. The data collected from each well was fit to a straight line and the resulting rates were used to calculate percent of control. Percent of control was plotted against compound concentration and IC50 values were determined using a four-parameter fit. Table 2 contains representative data for compounds disclosed herein. Representative date is in TABLE 2 (infra).

Example 3

Labchip Kinase ERK Assay

Compounds were tested in an enzymatic assay using human ERK-2 recombinantly expressed as an n-terminal 6-His fusion protein in *E. coli* and corresponding to aa 8-360. The substrate used was 5FAM-IPTSPITTTYFFFKKK-COOH (Caliper cat #760352). Test compounds were diluted in DMSO in 3-fold serial dilutions at 100× final concentrations. In addition to compound, the assay contained 50 mM Tris-HCl [pH 7.3], 10 mM MgCl2, 1 mM DTT, 0.01% Triton-X100, 3 nM ERK-2 enzyme, 0.375 µM peptide substrate and 25 µM ATP (corresponding to the observed $K_m$) for a total reaction volume of 25 µL. The assay was run at ambient temperature in a white 384-well polypropylene plate (Nunc, Inc of Naperville, Ill.; Cat. 267462) for 60 minutes then stopped by addition of EDTA. Percent substrate phosphorylated was determined by microfluidic separation using a Caliper LabChip 3000 instrument. Percent inhibition was plotted against compound concentration and $IC_{50}$ values were determined using a four-parameter fit.

Example 4

Cellular P90RSK(Ser380) Phosphorylation Assay

Inhibition of PMA-stimulated P90RSK(Ser380) phosphorylation was determined by the following in vitro cellular mechanistic assay, which comprises incubating cells with a compound for 1.5 hours and quantifying fluorescent pP90RSK(Ser380) signal on fixed cells and normalizing to GAPDH signal.

Materials and Methods: HepG2 cells were obtained from ATCC and grown in DMEM supplemented with 10% fetal bovine serum. Cells were plated in 96-well plates at 35,000 cells/well and allowed to attach overnight at 37° C./5% $CO_2$. Diluted compounds were then added at a final concentration of 0.5% DMSO. After 1.5 hour compound incubation, cells were stimulated with the addition of PMA (phorbol 12-myristate 13-acetate) at a final concentration of 100 ng/mL; the PMA stimulation was a 30-minute incubation at 37° C./5% CO2. After the 30-minute PMA stimulation, cells were washed with PBS and fixed in 3.7% formaldehyde in PBS at room temperature for 15-20 minutes. This was followed by another wash in PBS and then permeabilization in 100% MeOH at room temperature for 10-15 minutes. Following the permeabilization incubation, cells were washed in PBS/0.05% Tween-20, followed by a block in Odyssey blocking buffer (LI-COR Biosciences) for at least 1 hour. Antibodies to phosphorylated P90RSK(Ser380) (Cell Signaling #9335, rabbit monoclonal) and GAPDH (Fitzgerald 10R-G109a, mouse monoclonal) were added to the cells and incubated overnight at 4° C. pP90RSK(Ser380) antibody was used at a 1:250 dilution; GAPDH was used at a 1:10,000 dilution. After washing with PBS/0.05% Tween-20, the cells were incubated with fluorescently-labeled secondary antibodies (Anti-rabbit-Alexa Flour680, Invitrogen Cat#A21109; Anti-mouse-IRDye800CW, Rockland Inc. Cat#610-131-121) for 1 hour. Both secondary antibodies were used at a 1:1000 dilution. Cells were then washed and analyzed for fluorescence at both wavelengths using the Odyssey Infrared Imaging System (LI-COR Biosciences). Phosphorylated P90RSK(Ser380) signal was normalized to GAPDH signal. Representative date is in TABLE 2 (infra).

Example 5

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

What is claimed is:

1. A compound according to formula (I):

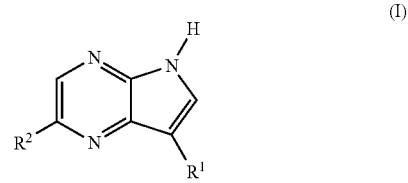

wherein $R^2$ is 5-methyl-1H-pyrazol-4-yl and $R^1$ is $N^1$-benzyl-pyrazol-4-yl.

2. A compound selected from the group consisting of:
   7-(1-benzyl-1H-pyrazol-4-yl)-2-pyridin-4-yl-5H-pyrrolo[2,3-b]pyrazine;
   7-[1-(3-fluoro-benzyl)-1H-pyrazol-4-yl]-2-pyridin-4-yl-5H-pyrrolo[2,3-b]pyrazine;
   7-[1-(3,4-difluoro-benzyl)-1H-pyrazol-4-yl]-2-pyridin-4-yl-5H-pyrrolo[2,3-b]pyrazine;
   7-[1-(1-phenyl-ethyl)-1H-pyrazol-4-yl]-2-pyridin-4-yl-5H-pyrrolo[2,3-b]pyrazine;
   7-(1-benzyl-1H-pyrazol-4-yl)-2-(2-methyl-pyridin-4-yl)-5H-pyrrolo[2,3-b]pyrazine;
   4-[7-(1-benzyl-1H-pyrazol-4-yl)-5H-pyrrolo[2,3-b]pyrazin-2-yl]-pyridin-2-ylamine;
   7-[1-(3-chloro-benzyl)-1H-pyrazol-4-yl]-2-pyridin-4-yl-5H-pyrrolo[2,3-b]pyrazine;
   7-(1-benzyl-1H-pyrazol-4-yl)-2-(2-methoxy-pyridin-4-yl)-5H-pyrrolo[2,3-b]pyrazine;
   7-(1-benzyl-1H-pyrazol-4-yl)-2-(2-fluoro-pyridin-4-yl)-5H-pyrrolo[2,3-b]pyrazine;
   7-[1-(3-methoxy-benzyl)-1H-pyrazol-4-yl]-2-pyridin-4-yl-5H-pyrrolo[2,3-b]pyrazine;
   7-[1-(3-fluoro-benzyl)-1H-pyrazol-4-yl]-2-(2-methyl-pyridin-4-yl)-5H-pyrrolo[2,3-b]pyrazine;
   7-[1-(3-chloro-4-fluoro-benzyl)-1H-pyrazol-4-yl]-2-pyridin-4-yl-5H-pyrrolo[2,3-b]pyrazine;
   7-[1-(3,4-dichloro-benzyl)-1H-pyrazol-4-yl]-2-pyridin-4-yl-5H-pyrrolo[2,3-b]pyrazine;
   7-[1-(2-fluoro-benzyl)-1H-pyrazol-4-yl]-2-pyridin-4-yl-5H-pyrrolo[2,3-b]pyrazine;
   7-[1-(4-fluoro-benzyl)-1H-pyrazol-4-yl]-2-pyridin-4-yl-5H-pyrrolo[2,3-b]pyrazine;
   4-{7-[1-(3-fluoro-benzyl)-1H-pyrazol-4-yl]-5H-pyrrolo[2,3-b]pyrazin-2-yl}-pyridin-2-ylamine; and
   7-[1-(3-methyl-benzyl)-1H-pyrazol-4-yl]-2-pyridin-4-yl-5H-pyrrolo[2,3-b]pyrazine; or
a pharmaceutically acceptable salt thereof.

3. A compound selected from the group consisting of:
   7-(1-benzyl-1H-pyrazol-4-yl)-2-(3,5-dimethyl-1H-pyrazol-4-yl)-5H-pyrrolo[2,3-b]pyrazine;
   7-(1-benzyl-1H-pyrazol-4-yl)-2-(3-methyl-1H-pyrazol-4-yl)-5H-pyrrolo[2,3-b]pyrazine;
   7-(1-benzyl-1H-pyrazol-4-yl)-2-(1,3-dimethyl-1H-pyrazol-4-yl)-5H-pyrrolo[2,3-b]pyrazine;
   7-(1-benzyl-1H-pyrazol-4-yl)-2-(1,5-dimethyl-1H-pyrazol-4-yl)-5H-pyrrolo[2,3-b]pyrazine;
   7-(1-benzyl-1H-pyrazol-4-yl)-2-(1,3,5-trimethyl-1H-pyrazol-4-yl)-5H-pyrrolo[2,3-b]pyrazine;
   7-[1-(3-fluoro-benzyl)-1H-pyrazol-4-yl]-2-(5-methyl-1H-pyrazol-4-yl)-5H-pyrrolo[2,3-b]pyrazine;
   2-(3,5-dimethyl-1H-pyrazol-4-yl)-7-[1-(3-fluoro-benzyl)-1H-pyrazol-4-yl]-5H-pyrrolo[2,3-b]pyrazine;
   7-[1-(3-chloro-4-fluoro-benzyl)-1H-pyrazol-4-yl]-2-(5-methyl-1H-pyrazol-4-yl)-5H-pyrrolo[2,3-b]pyrazine;
   7-[1-(3,4-dichloro-benzyl)-1H-pyrazol-4-yl]-2-(5-methyl-1H-pyrazol-4-yl)-5H-pyrrolo[2,3-b]pyrazine;

7-[1-(4-fluoro-benzyl)-1H-pyrazol-4-yl]-2-(5-methyl-1H-pyrazol-4-yl)-5H-pyrrolo[2,3-b]pyrazine;
7-[1-(4-methoxy-benzyl)-1H-pyrazol-4-yl]-2-(5-methyl-1H-pyrazol-4-yl)-5H-pyrrolo[2,3-b]pyrazine;
7-[1-(2,3-dichloro-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-[1-(3-trifluoromethoxy-benzyl)-1H-pyrazol-4-yl]-5H-pyrrolo[2,3-b]pyrazine;
7-[1-(2,4-difluoro-benzyl)-1H-pyrazol-4-yl]-2-(5-methyl-1H-pyrazol-4-yl)-5H-pyrrolo[2,3-b]pyrazine;
7-[1-(4-chloro-3-fluoro-benzyl)-1H-pyrazol-4-yl]-2-(5-methyl-1H-pyrazol-4-yl)-5H-pyrrolo[2,3-b]pyrazine;
7-[1-(2,3-Difluoro-benzyl)-1H-pyrazol-4-yl]-2-(5-methyl-1H-pyrazol-4-yl)-5H-pyrrolo[2,3-b]pyrazine;
2-(1,3-dimethyl-1H-pyrazol-4-yl)-7-[1-(3-fluoro-benzyl)-1H-pyrazol-4-yl]-5H-pyrrolo[2,3-b]pyrazine;
7-[1-(2-fluoro-benzyl)-1H-pyrazol-4-yl]-2-(5-methyl-1H-pyrazol-4-yl)-5H-pyrrolo[2,3-b]pyrazine;
7-[1-(3-chloro-benzyl)-1H-pyrazol-4-yl]-2-(5-methyl-1H-pyrazol-4-yl)-5H-pyrrolo[2,3-b]pyrazine;
7-[1-(4-chloro-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-[1-(1-phenyl-ethyl)-1H-pyrazol-4-yl]-5H-pyrrolo[2,3-b]pyrazine;
7-[1-(4-chloro-3-trifluoromethoxy-benzyl)-1H-pyrazol-4-yl]-2-(5-methyl-1H-pyrazol-4-yl)-5H-pyrrolo[2,3-b]pyrazine;
7-[1-(4-fluoro-3-methoxy-benzyl)-1H-pyrazol-4-yl]-2-(5-methyl-1H-pyrazol-4-yl)-5H-pyrrolo[2,3-b]pyrazine;
7-[1-(2-chloro-5-fluoro-benzyl)-1H-pyrazol-4-yl]-2-(5-methyl-1H-pyrazol-4-yl)-5H-pyrrolo[2,3-b]pyrazine;
7-[1-(3-fluoro-4-methoxy-benzyl)-1H-pyrazol-4-yl]-2-(5-methyl-1H-pyrazol-4-yl)-5H-pyrrolo[2,3-b]pyrazine;
7-[1-(3-methyl-benzyl)-1H-pyrazol-4-yl]-2-(5-methyl-1H-pyrazol-4-yl)-5H-pyrrolo[2,3-b]pyrazine;
7-[1-(2-chloro-4-fluoro-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-{1-[1-(3-trifluoromethyl-phenyl)-ethyl]-1H-pyrazol-4-yl}-5H-pyrrolo[2,3-b]pyrazine;
7-[1-(2-chloro-benzyl)-1H-pyrazol-4-yl]-2-(5-methyl-1H-pyrazol-4-yl)-5H-pyrrolo[2,3-b]pyrazine;
7-[1-(3-Methoxy-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-[1-(4-trifluoromethoxy-benzyl)-1H-pyrazol-4-yl]-5H-pyrrolo[2,3-b]pyrazine;
7-[1-(4-Methoxy-3-trifluoromethyl-benzyl)-1H-pyrazol-4-yl]-2-(5-methyl-1H-pyrazol-4-yl)-5H-pyrrolo[2,3-b]pyrazine;
7-{1-[1-(4-fluoro-phenyl)-ethyl]-1H-pyrazol-4-yl}-2-(5-methyl-1H-pyrazol-4-yl)-5H-pyrrolo[2,3-b]pyrazine;
7-[1-(2-methyl-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-[1-(2-nitro-benzyl)-1H-pyrazol-4-yl]-5H-pyrrolo[2,3-b]pyrazine;
2-{4-[2-(5-methyl-1H-pyrazol-4-yl)-5H-pyrrolo[2,3-b]pyrazin-7-yl]-pyrazol-1-ylmethy}-benzonitrile;
2-(5-methyl-1H-pyrazol-4-yl)-7-[1-(2-trifluoromethyl-benzyl)-1H-pyrazol-4-yl]-5H-pyrrolo[2,3-b]pyrazine;
(2-{4-[2-(5-methyl-1H-pyrazol-4-yl)-5H-pyrrolo[2,3-b]pyrazin-7-yl]-pyrazol-1-ylmethy}-phenyl)-methanol;
2-(5-methyl-1H-pyrazol-4-yl)-7-{1-[1-(2-trifluoromethyl-phenyl)-ethyl]-1H-pyrazol-4-yl}-5H-pyrrolo[2,3-b]pyrazine;
7-{1-[1-(2-chloro-phenyl)-ethyl]-1H-pyrazol-4-yl}-2-(5-methyl-1H-pyrazol-4-yl)-5H-pyrrolo[2,3-b]pyrazine;
2-(5-methyl-1H-pyrazol-4-yl)-7-[1-(2-trifluoromethoxy-benzyl)-1H-pyrazol-4-yl]-5H-pyrrolo[2,3-b]pyrazine;
2-(5-methyl-1H-pyrazol-4-yl)-7-{1-[(R)-1-(3-trifluoromethyl-phenyl)-ethyl]-1H-pyrazol-4-yl}-5H-pyrrolo[2,3-b]pyrazine;
7-{1-[(R)-1-(2-chloro-phenyl)-ethyl]-1H-pyrazol-4-yl}-2-(5-methyl-1H-pyrazol-4-yl)-5H-pyrrolo[2,3-b]pyrazine;
2-(5-methyl-1H-pyrazol-4-yl)-7-{1-[(S)-1-(3-trifluoromethyl-phenyl)-ethyl]-1H-pyrazol-4-yl}-5H-pyrrolo[2,3-b]pyrazine;
7-{1-[(S)-1-(2-chloro-phenyl)-ethyl]-1H-pyrazol-4-yl}-2-(5-methyl-1H-pyrazol-4-yl)-5H-pyrrolo[2,3-b]pyrazine;
7-[1-(1-methyl-1-phenyl-ethyl)-1H-pyrazol-4-yl]-2-(3-methyl-1H-pyrazol-4-yl)-5H-pyrrolo[2,3-b]pyrazine;
7-[1-(2,6-dichloro-benzyl)-1H-pyrazol-4-yl]-2-(5-methyl-1H-pyrazol-4-yl)-5H-pyrrolo[2,3-b]pyrazine;
7-[1-(2-chloro-6-fluoro-benzyl)-1H-pyrazol-4-yl]-2-(5-methyl-1H-pyrazol-4-yl)-5H-pyrrolo[2,3-b]pyrazine;
8-{4-[2-(5-methyl-1H-pyrazol-4-yl)-5H-pyrrolo[2,3-b]pyrazin-7-yl]-pyrazol-1-ylmethyl}-quinoline;
7-[1-(2,6-difluoro-benzyl)-1H-pyrazol-4-yl]-2-(5-methyl-1H-pyrazol-4-yl)-5H-pyrrolo[2,3-b]pyrazine;
7-[1-(3-fluoro-2-methyl-benzyl)-1H-pyrazol-4-yl]-2-(5-methyl-1H-pyrazol-4-yl)-5H-pyrrolo[2,3-b]pyrazine;
7-[1-(4-fluoro-2-methyl-benzyl)-1H-pyrazol-4-yl]-2-(5-methyl-1H-pyrazol-4-yl)-5H-pyrrolo[2,3-b]pyrazine;
7-[1-(2,4-dimethyl-benzyl)-1H-pyrazol-4-yl]-2-(5-methyl-1H-pyrazol-4-yl)-5H-pyrrolo[2,3-b]pyrazine;
7-[1-(4-methyl-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-[1-(3-trifluoromethyl-benzyl)-1H-pyrazol-4-yl]-5H-pyrrolo[2,3-b]pyrazine;
7-[1-(5-fluoro-2-methyl-benzyl)-1H-pyrazol-4-yl]-2-(5-methyl-1H-pyrazol-4-yl)-5H-pyrrolo[2,3-b]pyrazine;
7-[1-(2,5-dichloro-benzyl)-1H-pyrazol-4-yl]-2-(5-methyl-1H-pyrazol-4-yl)-5H-pyrrolo[2,3-b]pyrazine;
7-[1-(2-difluoromethoxy-benzyl)-1H-pyrazol-4-yl]-2-(5-methyl-1H-pyrazol-4-yl)-5H-pyrrolo[2,3-b]pyrazine;
7-[1-(2-fluoro-3-methyl-benzyl)-1H-pyrazol-4-yl]-2-(5-methyl-1H-pyrazol-4-yl)-5H-pyrrolo[2,3-b]pyrazine;
7-[1-(2,5-difluoro-benzyl)-1H-pyrazol-4-yl]-2-(5-methyl-1H-pyrazol-4-yl)-5H-pyrrolo[2,3-b]pyrazine;
4-fluoro-2-{4-[2-(5-methyl-1H-pyrazol-4-yl)-5H-pyrrolo[2,3-b]pyrazin-7-yl]-pyrazol-1-ylmethy}-benzonitrile;
7-[1-(2-fluoro-6-methoxy-benzyl)-1H-pyrazol-4-yl]-2-(5-methyl-1H-pyrazol-4-yl)-5H-pyrrolo[2,3-b]pyrazine;
7-[1-(2-chloro-3-trifluoromethyl-benzyl)-1H-pyrazol-4-yl]-2-(5-methyl-1H-pyrazol-4-yl)-5H-pyrrolo[2,3-b]pyrazine;
2-(5-methyl-1H-pyrazol-4-yl)-7-[1-(1-o-tolyl-ethyl)-1H-pyrazol-4-yl]-5H-pyrrolo[2,3-b]pyrazine;
2-(5-methyl-1H-pyrazol-4-yl)-7-[1-(2-methyl-3-trifluoromethyl-benzyl)-1H-pyrazol-4-yl]-5H-pyrrolo[2,3-b]pyrazine;
7-{1-[1-(2-fluoro-phenyl)-ethyl]-1H-pyrazol-4-yl}-2-(5-methyl-1H-pyrazol-4-yl)-5H-pyrrolo[2,3-b]pyrazine;
7-{1-[1-(2-methoxy-phenyl)-ethyl]-1H-pyrazol-4-yl}-2-(5-methyl-1H-pyrazol-4-yl)-5H-pyrrolo[2,3-b]pyrazine;
5-methyl-2-(3-methyl-1H-pyrazol-4-yl)-7-{1-[1-(3-trifluoromethyl-phenyl)-ethyl]-1H-pyrazol-4-yl}-5H-pyrrolo[2,3-b]pyrazine;

7-{1-[1-(3-fluoro-phenyl)-ethyl]-1H-pyrazol-4-yl}-2-(5-methyl-1H-pyrazol-4-yl)-5H-pyrrolo[2,3-b]pyrazine;
7-{1-[1-(4-chloro-phenyl)-ethyl]-1H-pyrazol-4-yl}-2-(5-methyl-1H-pyrazol-4-yl)-5H-pyrrolo[2,3-b]pyrazine;
2-(5-methyl-1H-pyrazol-4-yl)-7-[1-(1-p-tolyl-ethyl)-1H-pyrazol-4-yl]-5H-pyrrolo[2,3-b]pyrazine;
2-(5-methyl-1H-pyrazol-4-yl)-7-{1-[1-(4-trifluoromethyl-phenyl)-ethyl]-1H-pyrazol-4-yl}-5H-pyrrolo[2,3-b]pyrazine;
7-[1-(3,4-difluoro-benzyl)-1H-pyrazol-4-yl]-2-(5-methyl-1H-pyrazol-4-yl)-5H-pyrrolo[2,3-b]pyrazine; and
7-{1-[1-(2-chloro-phenyl)-propyl]-1H-pyrazol-4-yl}-2-(5-methyl-1H-pyrazol-4-yl)-5H-pyrrolo[2,3-b]pyrazine; or
a pharmaceutically acceptable salt thereof.

4. A compound selected from the group consisting of:
7-(6-chloro-5-methyl-pyridin-3-yl)-2-pyridin-4-yl-5H-pyrrolo[2,3-b]pyrazine;
7-(6-fluoro-5-methyl-pyridin-3-yl)-2-pyridin-4-yl-5H-pyrrolo[2,3-b]pyrazine;
7-(5-methyl-pyridin-3-yl)-2-pyridin-4-yl-5H-pyrrolo[2,3-b]pyrazine;
7-(5-methoxy-pyridin-3-yl)-2-pyridin-4-yl-5H-pyrrolo[2,3-b]pyrazine;
5-(2-pyridin-4-yl-5H-pyrrolo[2,3-b]pyrazin-7-yl)-pyridin-3-ylamine;
7-(6-cyclopropylmethoxy-pyridin-3-yl)-2-pyridin-4-yl-5H-pyrrolo[2,3-b]pyrazine;
(2-morpholin-4-yl-ethyl)-[5-(2-pyridin-4-yl-5H-pyrrolo[2,3-b]pyrazin-7-yl)-pyridin-2-yl]-amine;
7-(6-benzyloxy-pyridin-3-yl)-2-pyridin-4-yl-5H-pyrrolo[2,3-b]pyrazine;
7-(6-methoxy-pyridin-3-yl)-2-pyridin-4-yl-5H-pyrrolo[2,3-b]pyrazine;
7-(6-fluoro-pyridin-3-yl)-2-pyridin-4-yl-5H-pyrrolo[2,3-b]pyrazine;
2-pyridin-4-yl-7-pyridin-3-yl-5H-pyrrolo[2,3-b]pyrazine;
7-(5-fluoro-pyridin-3-yl)-2-pyridin-4-yl-5H-pyrrolo[2,3-b]pyrazine;
7-(2-fluoro-pyridin-3-yl)-2-pyridin-4-yl-5H-pyrrolo[2,3-b]pyrazine;
5'-(2-pyridin-4-yl-5H-pyrrolo[2,3-b]pyrazin-7-yl)-3,4,5,6-tetrahydro-2H-[1,2']bipyridinyl;
7-(2-chloro-pyridin-3-yl)-2-pyridin-4-yl-5H-pyrrolo[2,3-b]pyrazine;
7-(6-methyl-pyridin-3-yl)-2-pyridin-4-yl-5H-pyrrolo[2,3-b]pyrazine;
7-(6-morpholin-4-yl-pyridin-3-yl)-2-pyridin-4-yl-5H-pyrrolo[2,3-b]pyrazine;
5-(2-pyridin-4-yl-5H-pyrrolo[2,3-b]pyrazin-7-yl)-pyridin-2-ylamine;
pentanoic acid {5-[2-(1H-pyrazol-4-yl)-5H-pyrrolo[2,3-b]pyrazin-7-yl]-pyridin-3-ylmethy}-amide;
benzyl-{5-[2-(5-methyl-1H-pyrazol-4-yl)-5H-pyrrolo[2,3-b]pyrazin-7-yl]-pyridin-2-yl}-amine;
2-(5-methyl-1H-pyrazol-4-yl)-7-[6-(2-morpholin-4-yl-ethoxy)-pyridin-3-yl]-5H-pyrrolo[2,3-b]pyrazine;
4-fluoro-N-{5-[2-(1H-pyrazol-4-yl)-5H-pyrrolo[2,3-b]pyrazin-7-yl]-pyridin-3-ylmethy}-benzamide;
7-(6-cyclopropylmethoxy-pyridin-3-yl)-2-(5-methyl-1H-pyrazol-4-yl)-5H-pyrrolo[2,3-b]pyrazine;
{5-[2-(5-methyl-1H-pyrazol-4-yl)-5H-pyrrolo[2,3-b]pyrazin-7-yl]-pyridin-2-yl}-morpholin-4-yl-amine;
3-fluoro-N-{5-[2-(1H-pyrazol-4-yl)-5H-pyrrolo[2,3-b]pyrazin-7-yl]-pyridin-3-ylmethy}-benzamide;
2-(1H-pyrazol-4-yl)-7-pyridin-3-yl-5H-pyrrolo[2,3-b]pyrazine;
2-methyl-2H-pyrazole-3-carboxylic acid {5-[2-(1H-pyrazol-4-yl)-5H-pyrrolo[2,3-b]pyrazin-7-yl]-pyridin-3-ylmethy}-amide;
benzyl-methyl-{5-[2-(5-methyl-1H-pyrazol-4-yl)-5H-pyrrolo[2,3-b]pyrazin-7-yl]-pyridin-2-yl}-amine;
5-methyl-isoxazole-3-carboxylic acid {5-[2-(1H-pyrazol-4-yl)-5H-pyrrolo[2,3-b]pyrazin-7-yl]-pyridin-3-ylmethy}-amide;
pyrazine-2-carboxylic acid {5-[2-(1H-pyrazol-4-yl)-5H-pyrrolo[2,3-b]pyrazin-7-yl]-pyridin-3-ylmethy}-amide;
2,5-dimethyl-oxazole-4-carboxylic acid {5-[2-(1H-pyrazol-4-yl)-5H-pyrrolo[2,3-b]pyrazin-7-yl]-pyridin-3-ylmethy}-amide;
7-(6-benzyloxy-pyridin-3-yl)-2-(5-methyl-1H-pyrazol-4-yl)-5H-pyrrolo[2,3-b]pyrazine; and
(4-methyl-benzyl)-{5-[2-(5-methyl-1H-pyrazol-4-yl)-5H-pyrrolo[2,3-b]pyrazin-7-yl]-pyridin-2-yl}-amine;
or
a pharmaceutically acceptable salt thereof.

5. A pharmaceutical composition comprising a compound according to any one of claim 1, 2, 3, or 4, and at least one pharmaceutically acceptable carrier, excipient or diluent.

6. A method of inhibiting extracellular signal-regulated kinase activity in a cell comprising treating the cell with a compound according to any one of claim 1, 2, 3 or 4.

7. A method of inhibiting extracellular signal-regulated kinase activity in a patient comprising the step of administering to said patient a compound according to any one of claim 1, 2, 3, or 4.

* * * * *